United States Patent
Snell

(10) Patent No.: US 7,188,748 B2
(45) Date of Patent: Mar. 13, 2007

(54) VACUUM-PACKED DIAPER VENDING MACHINE

(75) Inventor: Alan Kay Snell, Idaho Falls, ID (US)

(73) Assignee: Diaperoos, LLC, Charlotte, NC (US)

( * ) Notice: Subject to any disclaimer, the term of this patent is extended or adjusted under 35 U.S.C. 154(b) by 68 days.

(21) Appl. No.: 10/907,396

(22) Filed: Mar. 31, 2005

(65) Prior Publication Data

US 2005/0189307 A1    Sep. 1, 2005

Related U.S. Application Data

(63) Continuation of application No. 10/907,333, filed on Mar. 29, 2005, now abandoned, which is a continuation-in-part of application No. 10/665,169, filed on Sep. 18, 2003.

(60) Provisional application No. 60/660,792, filed on Mar. 11, 2005, provisional application No. 60/451,433, filed on Mar. 4, 2003.

(51) Int. Cl.
*B06H 3/00* (2006.01)
*G07F 11/00* (2006.01)

(52) U.S. Cl. .................. 221/192; 221/232; 221/312 C; 312/242

(58) Field of Classification Search ................ 221/192, 221/232, 312 C; 312/242
See application file for complete search history.

(56) References Cited

U.S. PATENT DOCUMENTS

| | | | |
|---|---|---|---|
| 1,994,135 A | 3/1935 | Horowitz | |
| 2,145,137 A | 1/1939 | Sayers | |
| 2,764,201 A | 9/1956 | Whippo | |
| 2,764,859 A | 10/1956 | Hanselmann | |
| 2,834,459 A | 5/1958 | Rickard | |
| 2,935,828 A | 5/1960 | Mahaffy | |
| 3,343,683 A | 9/1967 | Bradford | |
| 3,442,686 A | 5/1969 | Jones | |
| 3,537,226 A | 11/1970 | LeVan | |
| 3,605,746 A | 9/1971 | Schaar | |
| 3,643,308 A | 2/1972 | Yamamoto | |
| 3,645,050 A | 2/1972 | Hammond | |
| 3,710,797 A | 1/1973 | Marsan | |
| 3,716,961 A | 2/1973 | Cope | |
| 3,794,033 A | 2/1974 | Ryan | |
| 3,795,355 A | 3/1974 | Gerstein | |

(Continued)

FOREIGN PATENT DOCUMENTS

GB    2292738 A * 3/1996

(Continued)

*Primary Examiner*—Patrick Mackey
*Assistant Examiner*—Michael Butler
(74) *Attorney, Agent, or Firm*—Chad D. Tillman; James D. Wright; Tillman Wright, PLLC

(57) ABSTRACT

A vending machine for dispensing absorbent articles includes at least one compartment for storing products for individual dispensing in response to selection by a consumer; and a plurality of products disposed within the at least one compartment for individually dispensing thereof to consumers. Each of the plurality of products disposed within the at least one compartment includes therein a volumetrically reduced absorbent article. Furthermore, a size of the product may be substantially smaller than a size of the absorbent article itself when not volumetrically reduced. The volumetrically reduced absorbent article may comprise a vacuum-packed diaper.

18 Claims, 15 Drawing Sheets

U.S. PATENT DOCUMENTS

| | | | |
|---|---|---|---|
| 3,824,759 A | 7/1974 | Finn | |
| 3,938,523 A | 2/1976 | Gilliland | |
| 3,943,930 A | 3/1976 | Schaar | |
| 3,958,693 A | 5/1976 | Greene | |
| 3,963,029 A | 6/1976 | Brooks | |
| 3,970,217 A * | 7/1976 | Culbertson et al. | 221/80 |
| 3,983,258 A | 9/1976 | Weaver | |
| 3,986,479 A | 10/1976 | Bonk | |
| 4,034,760 A | 7/1977 | Amirsakis | |
| 4,046,243 A * | 9/1977 | Valentine | 194/239 |
| 4,050,462 A | 9/1977 | Woon | |
| 4,056,919 A | 11/1977 | Hirsch | |
| 4,071,140 A | 1/1978 | Rattner | |
| 4,076,663 A | 2/1978 | Masuda | |
| 4,110,276 A | 8/1978 | DesMarais | |
| 4,143,672 A | 3/1979 | West | |
| RE30,045 E | 7/1979 | Greene | |
| 4,171,047 A | 10/1979 | Doyle | |
| 4,184,237 A | 1/1980 | Blankenship | |
| 4,221,221 A | 9/1980 | Ehrlich | |
| 4,242,854 A | 1/1981 | Nissen | |
| 4,265,070 A | 5/1981 | Mainberger | |
| 4,286,082 A | 8/1981 | Tsubakimoto | |
| 4,332,319 A | 6/1982 | Hurwood | |
| 4,550,548 A | 11/1985 | Owensby et al. | |
| 4,556,146 A | 12/1985 | Swanson | |
| 4,566,130 A | 1/1986 | Coates | |
| 4,573,608 A * | 3/1986 | Hansen | 221/92 |
| 4,575,990 A | 3/1986 | Bismarck | |
| 4,576,596 A | 3/1986 | Jackson | |
| 4,577,453 A | 3/1986 | Hofeler | |
| 4,585,448 A | 4/1986 | Enloe | |
| 4,594,835 A | 6/1986 | Gray | |
| 4,598,528 A | 7/1986 | McFarland | |
| 4,610,678 A | 9/1986 | Weisman | |
| 4,630,320 A | 12/1986 | Van Gompel | |
| 4,641,381 A | 2/1987 | Heran | |
| 4,646,362 A | 3/1987 | Heran | |
| 4,660,721 A | 4/1987 | Mykleby | |
| 4,663,915 A | 5/1987 | Van Erden | |
| 4,702,378 A | 10/1987 | Finkel | |
| 4,704,116 A | 11/1987 | Enloe | |
| 4,706,845 A | 11/1987 | Schnurer | |
| 4,735,316 A | 4/1988 | Froidh | |
| 4,736,847 A | 4/1988 | Wang | |
| 4,765,477 A | 8/1988 | Froidh | |
| 4,769,974 A | 9/1988 | Davis | |
| 4,790,840 A | 12/1988 | Cortina | |
| 4,798,603 A | 1/1989 | Meyer | |
| 4,801,005 A | 1/1989 | Hahn et al. | |
| 4,802,884 A | 2/1989 | Froidh | |
| 4,808,175 A | 2/1989 | Hansen | |
| 4,833,862 A | 5/1989 | Bortolani | |
| 4,859,518 A | 8/1989 | Schultz | |
| 4,874,340 A | 10/1989 | Smallwood | |
| 4,876,970 A * | 10/1989 | Bolduc | 108/35 |
| 4,886,512 A | 12/1989 | Damico | |
| 4,923,455 A | 5/1990 | Dean | |
| 4,928,829 A | 5/1990 | Di Bernardo | |
| 4,934,535 A | 6/1990 | Muckenfuhs | |
| 4,936,460 A | 6/1990 | Meyer | |
| 4,964,859 A | 10/1990 | Feldman | |
| 4,996,848 A | 3/1991 | Nelson et al. | |
| 5,016,778 A | 5/1991 | Reiland | |
| 5,042,227 A | 8/1991 | Merry | |
| 5,054,619 A | 10/1991 | Muckenfuhs | |
| 5,065,868 A | 11/1991 | Cornelissen et al. | |
| 5,071,414 A | 12/1991 | Elliott | |
| 5,087,253 A | 2/1992 | Cooper | |
| 5,111,934 A | 5/1992 | Morin | |
| 5,141,505 A | 8/1992 | Barrett | |
| 5,167,345 A * | 12/1992 | Bleeker | 221/17 |
| 5,172,629 A | 12/1992 | Merry | |
| 5,176,668 A | 1/1993 | Bernardin | |
| 5,192,606 A | 3/1993 | Proxmire | |
| 5,234,143 A | 8/1993 | Mahvi et al. | |
| 5,242,057 A | 9/1993 | Cook | |
| 5,255,817 A | 10/1993 | Reiland | |
| 5,261,531 A | 11/1993 | Nelves | |
| 5,293,756 A | 3/1994 | Nelson et al. | |
| 5,295,988 A | 3/1994 | Muckenfuhs | |
| 5,304,158 A | 4/1994 | Webb | |
| 5,326,300 A | 7/1994 | Sonders | |
| 5,361,905 A | 11/1994 | McQueeny | |
| 5,377,837 A | 1/1995 | Roussel | |
| 5,383,872 A | 1/1995 | Roessler | |
| 5,392,610 A | 2/1995 | Nelson et al. | |
| RE34,929 E | 5/1995 | Kristen | |
| 5,413,568 A | 5/1995 | Roach | |
| 5,439,154 A | 8/1995 | Delligatti | |
| 5,443,161 A | 8/1995 | Jonese | |
| 5,458,590 A | 10/1995 | Schleinz et al. | |
| 5,462,166 A | 10/1995 | Minton | |
| 5,509,915 A | 4/1996 | Hanson | |
| 5,514,067 A | 5/1996 | Schmidt | |
| 5,520,674 A | 5/1996 | Lavon | |
| RE35,276 E | 6/1996 | Chan | |
| 5,522,810 A | 6/1996 | Allen | |
| 5,564,261 A | 10/1996 | Kiner | |
| 5,590,509 A | 1/1997 | Esteves | |
| 5,620,098 A | 4/1997 | Boos et al. | |
| 5,638,661 A | 6/1997 | Banks | |
| 5,639,532 A | 6/1997 | Wells | |
| 5,651,778 A | 7/1997 | Melius | |
| 5,666,787 A | 9/1997 | Young | |
| 5,678,727 A | 10/1997 | Rice | |
| 5,692,606 A | 12/1997 | Elmaleh | |
| 5,702,379 A | 12/1997 | Preiss | |
| 5,706,950 A | 1/1998 | Houghton | |
| 5,722,774 A | 3/1998 | Hartz | |
| 5,766,389 A | 6/1998 | Brandon | |
| 5,792,131 A | 8/1998 | Mizutani | |
| 5,826,714 A | 10/1998 | Martin | |
| 5,829,230 A | 11/1998 | Hartz | |
| 5,842,571 A | 12/1998 | Rausch | |
| 5,860,714 A * | 1/1999 | Skord, Jr. | 312/242 |
| 5,878,551 A | 3/1999 | Curley et al. | |
| 5,891,125 A | 4/1999 | Plumley | |
| 5,897,542 A | 4/1999 | Lash | |
| 5,964,351 A | 10/1999 | Zander | |
| 5,967,665 A | 10/1999 | MacDonald | |
| 5,971,153 A | 10/1999 | Bauer | |
| 5,986,165 A | 11/1999 | Moder | |
| 6,004,307 A | 12/1999 | Colon | |
| 6,015,934 A | 1/2000 | Lee | |
| 6,026,957 A | 2/2000 | Bauer | |
| 6,028,240 A | 2/2000 | Wessel | |
| 6,040,494 A | 3/2000 | Kalentun | |
| 6,050,984 A | 4/2000 | Fujioka | |
| 6,070,397 A | 6/2000 | Bachhuber | |
| 6,079,562 A | 6/2000 | Bauer | |
| 6,092,658 A | 7/2000 | Pietrafesa | |
| 6,116,781 A | 9/2000 | Skeens | |
| 6,165,160 A | 12/2000 | Suzuki et al. | |
| 6,168,022 B1 | 1/2001 | Ward | |
| 6,213,304 B1 | 4/2001 | Juliussen | |
| 6,229,061 B1 | 5/2001 | Dragoo | |
| 6,247,612 B1 * | 6/2001 | Kaufman | 221/312 C |
| 6,260,211 B1 | 7/2001 | Rajala | |
| 6,263,814 B1 | 7/2001 | O'Connor | |
| 6,264,972 B1 | 7/2001 | Drury | |
| 6,297,424 B1 | 10/2001 | Olson | |
| 6,298,993 B1 | 10/2001 | Kalozdi | |
| 6,316,687 B1 | 11/2001 | Davis | |

| | | | | | | |
|---|---|---|---|---|---|---|
| 6,318,555 | B1 | 11/2001 | Kuske et al. | 2003/0223652 A1 | 12/2003 | Schneider |
| 6,321,513 | B1 | 11/2001 | Meixner | 2004/0092901 A1 | 5/2004 | Reece |
| 6,364,101 | B1 | 4/2002 | Schultz | 2004/0159658 A1 | 8/2004 | McLaughlin |
| 6,370,843 | B1 | 4/2002 | Bercaits | 2004/0167489 A1 * | 8/2004 | Kellenberger et al. .. 604/385.01 |
| 6,387,085 | B1 | 5/2002 | Van Gompel | 2004/0167490 A1 * | 8/2004 | Nelson et al. ......... 604/385.01 |
| 6,408,872 | B1 | 6/2002 | Skeens | 2004/0167493 A1 | 8/2004 | Jarpenberg |
| 6,423,045 | B1 | 7/2002 | Wise | 2004/0168947 A1 | 9/2004 | McDonald |
| 6,443,938 | B1 | 9/2002 | Vogt | 2004/0172002 A1 | 9/2004 | Nelson |
| 6,454,095 | B1 | 9/2002 | Brisebois | 2004/0173490 A1 | 9/2004 | Otsubo |
| 6,458,110 | B1 | 10/2002 | Lavon | 2004/0176735 A1 | 9/2004 | Snell |
| 6,475,199 | B1 | 11/2002 | Gann | 2004/0238393 A1 | 12/2004 | Ohi et al. |
| 6,497,692 | B1 | 12/2002 | Tameishi | 2005/0011166 A1 | 1/2005 | Germano |
| 6,500,160 | B2 | 12/2002 | Mizutani | 2005/0015052 A1 | 1/2005 | Klippen |
| 6,502,695 | B1 | 1/2003 | Kim | 2005/0085780 A1 | 4/2005 | Corlett |
| 6,519,505 | B2 * | 2/2003 | Formon ................ 700/232 | 2005/0085781 A1 | 4/2005 | Corlett |
| 6,520,334 | B1 | 2/2003 | Hoover | 2005/0138894 A1 | 6/2005 | Snell |
| 6,528,766 | B1 | 3/2003 | Parks | 2005/0138896 A1 | 6/2005 | Snell |
| 6,540,084 | B2 | 4/2003 | Silvers | 2005/0139503 A1 | 6/2005 | Snell |
| 6,575,191 | B2 | 6/2003 | Skeens | 2005/0143700 A1 | 6/2005 | Snell |
| 6,575,947 | B1 | 6/2003 | Tameishi | 2005/0143701 A1 | 6/2005 | Snell |
| 6,581,641 | B2 | 6/2003 | Skeens | 2005/0143702 A1 | 6/2005 | Snell |
| 6,630,237 | B2 | 10/2003 | Rivett | 2005/0143704 A1 | 6/2005 | Snell |
| 6,634,384 | B2 | 10/2003 | Skeens | 2005/0143705 A1 | 6/2005 | Snell |
| 6,635,797 | B2 | 10/2003 | Olson et al. | 2005/0143706 A1 | 6/2005 | Snell |
| 6,702,798 | B2 | 3/2004 | Christoffel et al. | 2005/0155327 A1 | 7/2005 | Snell |
| 6,723,080 | B1 * | 4/2004 | Habib et al. ........... 604/385.06 | 2005/0155328 A1 | 7/2005 | Snell |
| 6,892,884 | B1 | 5/2005 | Fernandez | 2005/0155875 A1 | 7/2005 | Snell |
| 2001/0045372 | A1 | 11/2001 | Curley et al. | 2005/0155892 A1 | 7/2005 | Snell |
| 2002/0056655 | A1 | 5/2002 | Cottingham | 2005/0155893 A1 | 7/2005 | Snell |
| 2002/0078665 | A1 | 6/2002 | Salman | 2005/0155894 A1 | 7/2005 | Snell |
| 2002/0079246 | A1 | 6/2002 | Ling | 2005/0155895 A1 | 7/2005 | Snell |
| 2002/0117419 | A1 | 8/2002 | Tippey | 2005/0155896 A1 | 7/2005 | Snell |
| 2002/0125171 | A1 | 9/2002 | Kuske | 2005/0155897 A1 | 7/2005 | Snell |
| 2002/0170275 | A1 | 11/2002 | Salman | 2005/0155898 A1 | 7/2005 | Snell |
| 2002/0179478 | A1 | 12/2002 | Silvers | 2005/0155899 A1 | 7/2005 | Snell |
| 2003/0010415 | A1 | 1/2003 | Szuszkiewicz | 2005/0155900 A1 | 7/2005 | Snell |
| 2003/0015453 | A1 | 1/2003 | Ganey | 2005/0159718 A1 | 7/2005 | Snell |
| 2003/0029740 | A1 | 2/2003 | Caveness | 2005/0159723 A1 | 7/2005 | Snell |
| 2003/0062375 | A1 * | 4/2003 | Christensen et al. ......... 221/46 | 2005/0165377 A1 | 7/2005 | Klitzke |
| 2003/0065300 | A1 | 4/2003 | Suga | 2005/0189307 A1 | 9/2005 | Snell |
| 2003/0065302 | A1 | 4/2003 | Kuroda | | | |
| 2003/0073970 | A1 | 4/2003 | Suga | | | |
| 2003/0102245 | A1 | 6/2003 | Wang | | | |
| 2003/0153891 | A1 | 8/2003 | Molee | | | |
| 2003/0183550 | A1 | 10/2003 | DiLiberto | | | |

FOREIGN PATENT DOCUMENTS

GB  2300184 A  * 10/1996

* cited by examiner

VACUUM-PACKED DIAPER VENDING MACHINE

CROSS-REFERENCE TO RELATED APPLICATIONS

This application is a continuation of and claims priority to U.S. patent application Ser. No. 10/907,333, filed Mar. 29, 2005 now abandoned, which is hereby incorporated herein by reference, and which application is: (1) a continuation-in-part of and claims priority to U.S. patent application Ser. No. 10/665,169, filed Sep. 18, 2003, which is hereby incorporated herein by reference, and which application is a nonprovisional of and claims priority to U.S. Provisional Patent Application No. 60/451,433, filed Mar. 4, 2003, which is hereby incorporated herein by reference; and (2) a nonprovisional application of and claims priority to U.S. patent application Ser. No. 60/660,792, filed on Mar. 11, 2005, which is hereby incorporated herein by reference. Moreover, the '169 Application published on Sep. 9, 2004, as Patent Application Publication No. US 2004/0176735 A1, which publication also is incorporated herein by reference.

BACKGROUND

The present invention relates generally to disposable packaged diapers and related infant and incontinent adult care accessories. More particularly, the present invention relates to a reduced size packaged diaper, and related infant and incontinent adult care accessories and kits.

Diapers are generally a necessity for very young children and incontinent adults. Individuals incapable of controlling the release of bodily waste in a manner sufficiently reliable to enable the use of restroom facilities, and those caring for such individuals, typically need to carry extra disposable diapers and changing accessories. This is typically because it is difficult to predict when a diaper worn by an individual may need to be changed. Caretakers of babies and others requiring diapers often carry spare, clean diapers for this reason.

Many of the following discussions and examples are directed to use of diapers in infant care. However, it will be apparent that many of the same considerations apply to use of diapers for non-infant, incontinent persons.

Storage and carriage of clean diapers is often inconvenient. For instance, disposable diapers are generally rather bulky items not given to easy storage or carriage in a purse, pocket, or otherwise about the person. In addition, the problem can be acerbated in that diapers can be subject to expansion from the typically somewhat compressed state in which they are normally provided to consumers, especially in circumstances where the diapers are subject to contact with other items within a storage bag. For example, many disposable diapers are provided in a bi-fold configuration meant to minimize the space taken in storing the diaper. However, after being removed from their original packaging, bi-fold diapers often unfold or otherwise expand to consume an even larger storage space. Thus, disposable diapers can become more bulky and difficult to carry than when in their nominal, packaged condition.

In addition, it is often the case that it is not sufficient to simply change a soiled diaper and replace it with a clean diaper. For instance, cleaning of the individual who wore the diaper may need to be performed with diaper accessories, such as moist wipes. Also, it may be necessary to apply ointment or powder to the individual wearing the diaper to treat or prevent incidents of diaper rash or other skin conditions. Due to these considerations, caretakers of individuals requiring diapers often carry clean diapers and diaper changing accessories in a dedicated container, is often referred to as a "diaper bag." By doing so, when it becomes necessary to change a diaper, all of the materials needed by the caretaker are available in one location.

While a conventional diaper bag provides a dedicated container in which diapers and diaper accessories can be stored and carried, the requirement of carriage of a diaper bag often adds to the difficulty of a caretaker's responsibility. For example, parents of young children often must carry a purse or briefcase for the parent's own needs. In addition to this, the parent may need to carry the young child; and, of course, the child's diaper bag. This can leave the parent with no free hands for other tasks.

While conventional clean diapers and diaper changing accessories can be stored and carried in other carrying containers such as purses, backpacks, briefcases, etc., the bulky nature of conventional disposable diapers results in the diapers occupying a relatively large space within the carrying container. In addition, diaper changing accessories such as moist wipes, ointment, powder, etc., add to the space consumed by conventional clean diapers and can be difficult to locate among other items stored in the backpack, purse, case, or the like.

Where the diapers being carried by the caretaker are for bottle feeding infants, the problems discussed above are further exacerbated by the need to carry materials for feeding the baby. In addition to the accoutrement necessary to attending to changing the baby's diaper, things such as bottles, nipples, containers of formula or milk, etc., generally must also be carried.

SUMMARY OF THE INVENTION

It has been recognized that it would be advantageous to develop a packaged diaper that requires a relatively small amount of storage space. In addition, it has been recognized that it would be advantageous to develop a diaper and related accessory kit that consumes a relatively small amount of space while providing substantially all of the materials necessary to change an individual's diaper. It has also been recognized that it would be advantageous to develop an infant care kit that consumes a relatively small amount of space while providing substantially all of the materials necessary to feed the infant and change the infant's diaper.

The invention provides a packaged diaper, including a diaper, having a first, nominal size, and a second, reduced size, the reduced size of the diaper being convenient for carriage and storage of the diaper. An encasement can also be provided, in which the diaper can be disposed in the second, reduced size. The encasement can confine the diaper so that the diaper is retained in its reduced size by the encasement and so that the diaper is returned to its nominal size upon opening of the encasement.

In accordance with another aspect of the invention, a packaged diaper is provided, including a diaper, having a first, nominal configuration characterized by a nominal length, width and height, and a second, reduced configuration characterized by a second, reduced length, width and height. The reduced length can be between about 2 inches to about 4 inches, the reduced width can be between about 1.0 inch to about 2.5 inches, and the reduced thickness can be between about 0.5 inches to about 1.5 inches. An encasement can also be provided, in which the diaper can be disposed and retained in the second, reduced configuration.

In accordance with another aspect of the invention, a packaged diaper is provided, including a diaper, having a first, nominal size and shape, and a reduced, substantially cylindrical size and shape. The reduced, substantially cylindrical shape can have a diameter between about 0.5 inches to about 1.5 inches and a length between about 2 inches to about 4 inches. An encasement can also be provided, in which the diaper can be disposed and retained in the reduced, substantially cylindrical shape.

In accordance with another aspect of the invention, a packaged diaper is provided, including a diaper having a first, nominal volumetric configuration characterized by a nominal length and width of the diaper, and a second, reduced volumetric configuration characterized by a reduced length and width of the diaper. An encasement can also be provided, the encasement formed of a substantially air impermeable material. The diaper can be disposed in the encasement in the second, reduced volumetric configuration and the encasement can be at least partially evacuated of air so as to contain the diaper in at least a partial vacuum state. Differential pressure within and without the encasement can maintain the second, reduced volumetric configuration of the diaper and the encasement can be sealed to confine the diaper so that the diaper is returned to its nominal volumetric configuration upon opening of the encasement.

In accordance with another aspect of the invention, a method of packaging a diaper is provided and includes the steps of: a) folding the diaper at least once along both a lengthwise and a crosswise aspect of the diaper; b) disposing the folded diaper within an encasement comprised of a substantially air impermeable material; c) evacuating air from the encasement and the folded diaper; and d) sealing the encasement to maintain a vacuum created within the encasement and the folded diaper.

In accordance with another aspect of the invention, a method of packaging a diaper is provided and includes the steps of: a) volumetrically reducing a size of the diaper to a size convenient for carriage and storage of the diaper; b) disposing the volumetrically reduced diaper within an encasement; and c) maintaining the volumetrically reduced size of the diaper with the encasement.

In a more detailed aspect, the encasement can facilitate this by virtue of its hoop strength and/or by means of a pressure differential acting upon the encasement.

In accordance with another aspect of the invention, a diaper changing kit is provided and includes a packaged diaper in accordance with one or more previously set forth aspects of the invention, at least one diaper accessory, and a container in which the packaged diaper and the diaper accessory can be disposed. In a more detailed aspect, the accessory can be one or more of: a) a moistened wipe; b) baby powder; c) a medicament; d) a swab; e) a lotion; and, a disposal bag for a dirty diaper. In another more detailed aspect the container can be configured to have a first, oversized size and shape and a second smaller size and shape, and to also function as a disposal container for a dirty diaper.

In accordance with another aspect of the invention, an infant care kit is provided and includes a diaper, a diaper accessory, a portion of infant food and an infant feeding assembly. The infant feeding assembly can have a hollow body and a nipple portion couplable thereto. The diaper, diaper accessory, and portion of infant food can each be disposed in the infant feeding assembly. The infant feeding assembly can be configured to: i) contain each of the diaper, at least one diaper accessory and at least one portion of infant food; and ii) upon removal of the diaper and diaper accessory, receive the portion of infant food within the hollow body and deliver the infant food to an infant with the food delivery device. In a more detailed aspect a warming pack can also be provided for warming the infant food.

In accordance with another aspect of the invention, a packaged diaper is provided and includes a diaper, having a first, nominal size, and a second, reduced size, the reduced size of the diaper being convenient for carriage and storage of the diaper. A restraint can also be provided, in which the diaper can be disposed in the second, reduced size. The restraint can confine the diaper so that the diaper is retained in its reduced size by the restraint and so that the diaper is returned to its nominal size upon opening of the restraint.

In accordance with another aspect of the invention, a packaged diaper is provided and includes a densified diaper volumetrically reduced to a second reduced volume and increased density from a first greater volume and lesser nominal density. The reduction of the diaper can entail reduction in one or more dimensions. An encasement can also be provided in which the diaper can be disposed in the second reduced volume. The encasement can confine the diaper so that the diaper is retained in the reduced volume by the encasement.

In accordance with another aspect of the invention, an expandable diaper is provided and includes a diaper being reduced to a second, reduced size from a first, nominal size, the reduced size of the diaper being reduced in at least two dimensional directions relative to the nominal size. An encasement can also be provided in which the diaper can be disposed in the second, reduced size. The encasement can confine the diaper so that the diaper is retained in the reduced size by virtue of the encasement.

In accordance with another aspect of the invention, a packaged diaper is provided and includes a diaper, having a first, nominal size, and a second, reduced size, the reduced size of the diaper being convenient for carriage and storage of the diaper. A restraint can also be provided in which the diaper can be disposed in the second, reduced size. The restraint can confine the diaper so that the diaper is retained in its reduced size by the restraint and so that the diaper is returned to its nominal size upon opening of the restraint.

In addition to the foregoing, one or more other aspects of the present invention as found in the provisional patent application incorporated by reference above each relates to a method for miniaturizing a diaper. In this respect, a preferred such method comprises: folding a diaper within a jig; transferring the folded compressed diaper from the jig using a clamping apparatus; inserting the folded compressed diaper into a pliable bag; and vacuum sealing the bag thereby further miniaturizing the diaper within the bag. The miniaturized finished product preferably fits into a conveniently sized box for eliminating the bulky nature of carrying bulky diapers within a purse or other carrying case. Furthermore, the finished product is condensed down to a firm and hard exterior surface, and may be disguised in appearance, for example, to look like a candy bar instead of a baby diaper or an adult diaper. The miniaturization process can be readily adapted to mechanical application for automatic manufacturing assembly line runs.

Additional features and advantages of the invention will be apparent from the detailed description which follows, taken in conjunction with the accompanying drawings, which together illustrate, by way of example, features of the invention.

DETAILED DESCRIPTION

Figure 1A:
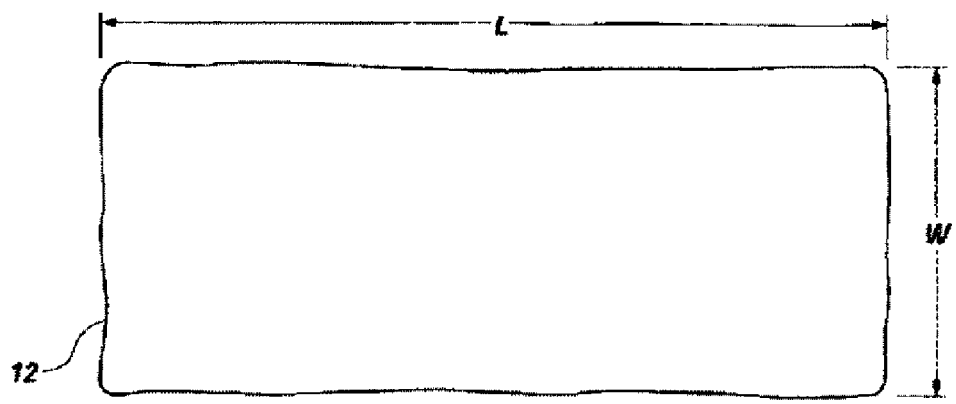
FIG. 1A is a top view of a diaper in a nominal configuration in accordance with an embodiment of the present invention.
Figure 1B:
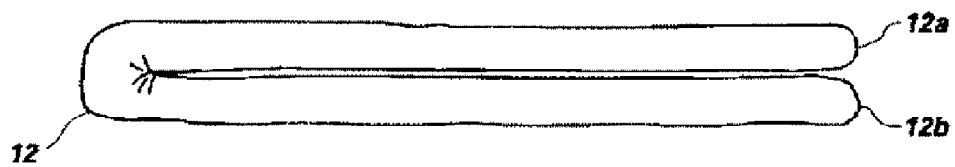
FIG. 1B is a side view of the diaper of FIG. 1A.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1A through 2B, an exemplary packaged, disposable, diaper 10 is sized and shaped to consume a considerably smaller volume and be more conveniently shaped than conventional disposable diapers. As illustrated, the packaged diaper 10 begins as a diaper 12 nominally sized and shaped in accordance with conventional diapers. The diaper can be one of a variety of types known to those in the art, and can be formed of a variety of materials. The diaper can be disposable or non-disposable (i.e., resusable).

As shown in FIG. 1A, the diaper begins with a first, nominal volumetric configuration characterized by a nominal length L and nominal width W of the diaper. As used herein, the term "nominal" is understood to mean to be the normal, post manufacturing state in which it is ready to be unfolded and worn, in reference to the various dimensions of the diaper. Thus, the diaper 12 can have a first size having a height, width and length of nominal size, such as conventionally provided to consumers. While not so required, the diaper 12 can include upper 12a and lower 12b portions, which can correspond to a front and back of the diaper. Many conventional diapers are provided with a front and back portion of different configuration.

Figure 2A:
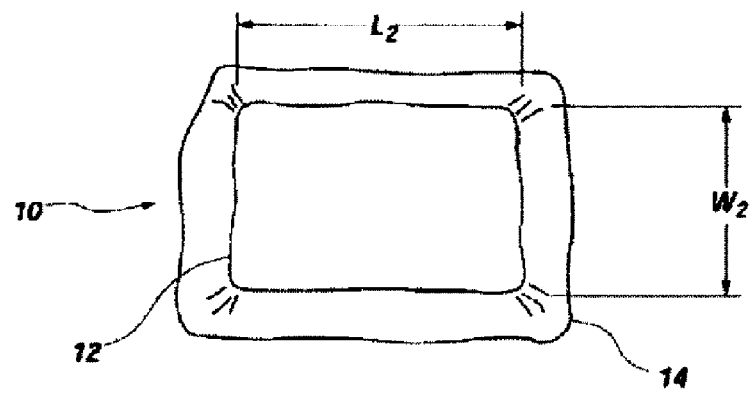
FIG. 2A is a top view of a diaper in a volumetrically reduced configuration in accordance with an embodiment of the present invention.
Figure 2B:
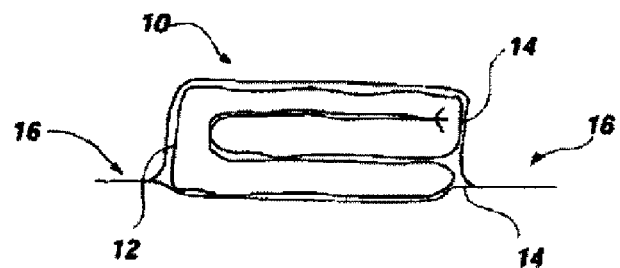
FIG. 2B is a side view of the diaper of FIG. 2A.

As shown in FIGS. 2A and 2B, an example of a packaged diaper 10, after being prepared in accordance with the description to follow below, includes a diaper 12 having a second, reduced volumetric configuration characterized by a reduced length $L_2$ and width $W_2$ of the diaper 12. The reduced volumetric configuration can differ from the nominal volumetric configuration in width, height, thickness, volume and overall size. As will be appreciated from the figures, not only is the volume of the packaged diaper reduced overall, but in the example embodiment at least two of the: 1) length; 2) width; and, 3) height, can also be reduced. Thus, the diaper can be reduced in volumetric configuration to consume much less space than the diaper consumes when in the nominal configuration.

As mentioned, the diaper 12 can be disposed in an encasement 14, which can be formed of a substantially air impermeable material. By disposing the diaper in the encasement in the second, reduced volumetric configuration, a packaged diaper is provided that consumes much less space than the when in its nominal configuration. By "substantially air impermeable," what is meant is that the permeability is low enough that the product has a reasonable shelf life without significant expansion.

As an example, it has been found that by drawing a vacuum down to about 5 Mbar at room temperature and pressure at a location about 5,000 feet elevation above mean sea level, the volume of the diaper can be reduced to as little as ⅓ or ¼ that of the nominal volume. Similar results are to be expected at locations of different elevation. However, as is known, at lower elevations a greater vacuum can be drawn to allow for subsequent transportation of the packaged product to higher elevations. For example, vacuum packaging using a vacuum down to 1 or 2 Mbar is common at lower elevations. Thus, in the space required to store one conventional diaper, three, four, or more, diapers packaged in accordance with the invention can be stored. The reduced volume packaged diapers are not only advantageous in reducing storage space, the space required for packaging, shipping, etc., is also reduced, leading to considerable cost savings in associated processes.

While the reduced volume configuration can be created and maintained in a number of ways, in the embodiment shown in FIGS. 2A and 2B, the packaged diaper 10 includes encasement 14, which can encompass the reduced volume diaper. Once the diaper 12 is disposed within the encasement, the encasement can be at least partially evacuated of air so as to contain the diaper in at least a partial vacuum state. The evacuation of air from within the diaper and encasement can be done in a number of ways, such as by conventional vacuum-packing methods.

For example, according to at least one conventional vacuum-packing method known to those skilled in the relevant art, an article to be vacuum-packed is inserted into an unsealed encasement formed of a substantially air impermeable flexible material. The unsealed encasement with the article therein is then placed onto the deck of a vacuum-sealing machine. The lid of the machine is then lowered establishing a seal with the deck and to define a chamber between the deck and the lid with the unsealed encased article within the chamber. A pumping system then evacuates ambient air from the chamber creating at least a partial vacuum state within the chamber and within the interior space of the unsealed encasement with the article therein. Sealing bars then seal the encasement to maintain at least a partial vacuum state therein. Ambient air pressure is then restored to the chamber effecting a pressure differential across the sealed encasement. Insofar as the article within the sealed flexible encasement is compressible, the pressure differential acts upon the encasement to compress the article and maintains the article in a reduced volume that is less than the volume of the article at the time the encasement was sealed (before ambient air pressure was restored to the chamber). The lid of the machine is then raised and the vacuum-packed article is available for removal from the machine.

Upon evacuation of air from the encasement, the encasement can be sealed, for example at an edge portion 16 to maintain the vacuum within the encasement and diaper 12. In this manner a differential pressure can be created within and without the encasement to maintain the second, reduced volumetric configuration of the diaper. While the encasement is shown in FIG. 2B as sealed at an edge portion 16, it will be understood that the encasement can be sealed conventionally in a variety of ways in a variety of locations.

As the encasement 14 configured to confine the diaper 12 is unsealed, the diaper is able to return to its nominal volumetric configuration. That is, user can cut, tear, remove a portion of the encasement, or otherwise break the airtight seal of the encasement; after which, the diaper 12 will no longer be subject to confining force due to the encasement and/or a pressure differential. Unopposed rebound forces in the materials from which the diaper is made will tend to return it to its nominal configuration. The encasement can include a means to facilitate opening, such as a notch or another intentionally formed discontinuity (not shown) provided in the encasement to aid in opening the encasement. In one embodiment a tear-away band, or the like, provided with a grasping tab (not shown) can be provided to facilitate opening therefrom by rupturing the encasement as it is pulled away therefrom. One of many other well known ways to provide a more easily broken-open encasement can be used to facilitate opening the packaging.

As described in further detail below, the reduced volumetric configuration can be achieved in a number of ways, and in the embodiment shown in FIGS. 2A and 2B, the volumetrically reduced configuration is created by foldingly reducing a length and width of the diaper 12; increasing its thickness. The folded diaper is then vacuum-packed to reduce its thickness (as well as its width and length to a lesser extent). As used herein, the term "foldedly reduced" is meant to indicate the case wherein a diaper is folded or rolled over or under itself to thereby reduce a dimension of the diaper.

While the final size of the reduced volume diaper can vary, in one aspect of the invention, the reduced length and width can each be less than about ½ of the nominal length and width, respectively, of the diaper. In another aspect of the invention, the foldedly reduced length of the diaper can be less than about ⅓ and/or ¼ of the nominal length of the diaper. In this manner, as shown by comparing FIGS. 1A and 1B with FIGS. 2A and 2B, the overall width and length of the diaper can be substantially reduced. While a height dimension, corresponding to thickness, may be increased, it is not increased to exceed the width or the length of the diaper. This results in a more convenient and compact size overall.

The inventor has found that a conventional size 6 diaper can be reduced in size and volume from a nominal size of approximately 9" long by 4.5" wide by ¼" to 1" in height/thickness (depending on expansion after removal from conventional packaging) to a reduced size of approximately 3.5" long by 2.25" wide by 1" in height. In the embodiment shown in FIGS. 2A and 2B, the packaged diaper 10 can include a reduced volumetric shape configuration which comprises a substantially rectangular shape, although other shapes are contemplated as well, as discussed in further detail below. In this manner, the packaged diaper can be easily carried, handled and stored within a purse, pocket, bag or other place or containment for carriage.

The packaged diaper in a densified state can thus be made pocket sized, or pocketable. As used herein that means that it is conveniently sized for carriage, for example about the size of a conventional cigarette package or smaller. One way to characterize this is that two of the three dimensions of height width and length, when added together, are less than 10 cm, and the greatest of the three does not exceed 10 centimeters. That said, all pocket sized items may not strictly fit this definition, but it is a definite guide in understanding what is meant by the term as used herein.

It will be appreciated that in this example the present invention provides a compact, efficiently sized packaged diaper that requires substantially less space than conventionally packaged diapers. The present invention can be advantageously utilized by a variety of persons, including incontinent minors and adults, and caretakers of individuals requiring diapers.

For example, parents of young children will benefit from the invention in that one or more diapers 10 can be easily stored in a pocket, or within a purse, briefcase, backpack or other storage bag and consume relatively little space. Similar benefits can be obtained with regard to incontinent adults, as adult diapers are generally even more bulky and difficult to store and carry than are smaller, children's diapers. Also, incontinent adults who may be otherwise embarrassed by having to carry spare clean diapers will likely find the packaged diapers in accordance with the invention to be much more discreetly transportable, and therefore the carriage of such spare diapers much less noticeable by others.

In addition, in one aspect of the invention a packaged, pocketable diaper is provided and can include an encasement configured to encase and confine a diaper disposed therein. A diaper can be disposed within the encasement to be confined by the encasement in a size that is volumetrically reduced relative to a nominal size of the diaper. The volumetrically reduced size of the diaper is characterized in that the diaper is pocketable upon a person of an individual. As used herein, the term "pocketable" is to be understood to indicate a configuration of the diaper in which the diaper can be easily placed within and removed from a pocket of an item of clothing or accessories worn or carried by individuals. For example, the pocketable diaper can be held within a shirt, jacket or pants pocket or stored or carried in a handbag, purse or briefcase, etc., and can be substantially undetectable by other individuals. In this manner, an incontinent adult can carry the pocketable diaper without worrying that others will be aware that the diaper is being carried. Also, an adult caretaker of an infant can carry a diaper for the infant in a manner that does not detract from a physical appearance of the adult and does not require additional baggage.

In several embodiments of the invention, a reduced diaper is provided. The reduced diaper is densified by volumetric reduction from a first greater volume and lesser nominal density to a second reduced volume and increased density. An encasement can also be included and the diaper can be disposed in the encasement in the second reduced volume. The encasement can thereby confine the reduced diaper so that the diaper is retained in the reduced volume by the encasement. The volumetric reduction can entail dimensional reductions in width, thickness, length, and diameter. In this manner, a volumetrically reduced, space-efficient densified diaper is provided that can be easily stored and carried by an individual in a discreet manner. Upon release of the reduced diaper from the encasement, the diaper can be volumetrically expanded and used in the same manner as conventionally packaged diapers.

As used herein, the term "encasement" is to be understood to encompass a broad range of materials and configurations for containing or restraining or enclosing a volumetrically reduced diaper. For example, the encasement may completely encompass a diaper and hold the diaper under a vacuum seal or other pressure differential. In addition, the encasement may only partially encompass the diaper to maintain the compressed state of the diaper. Moreover, it is intended to be understood herein to be synonymous with restraint (as discussed below) or enclosure, or containment, in this context. The salient point being that it constrains, by some means, the densified diaper from expanding. Other encasements besides the examples shown can also be utilized, as would occur to one skilled in the art.

Figure 3A:
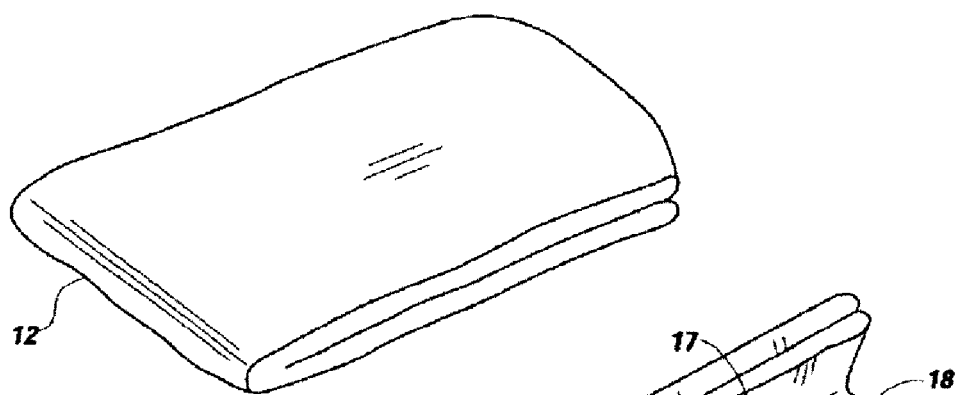
FIG. 3A is a perspective view of a diaper in accordance with an embodiment of the invention.
Figure 3B:
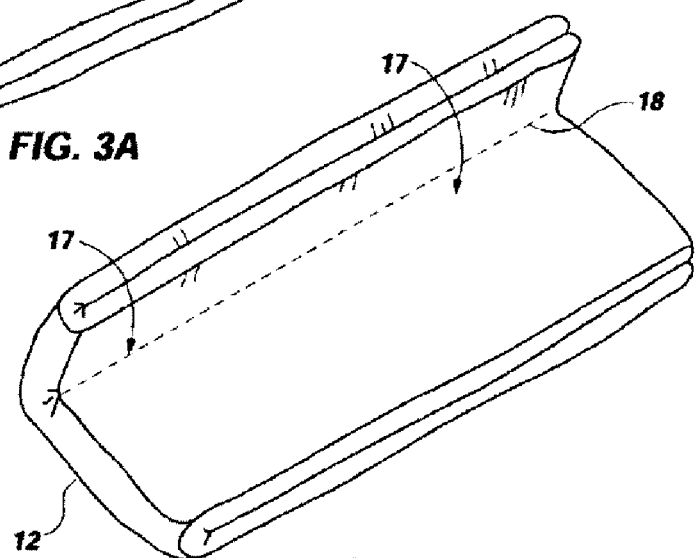
FIG. 3B is a perspective view of the diaper of FIG. 3A in the process of folding the diaper along a lengthwise aspect of the diaper.
Figure 3C:
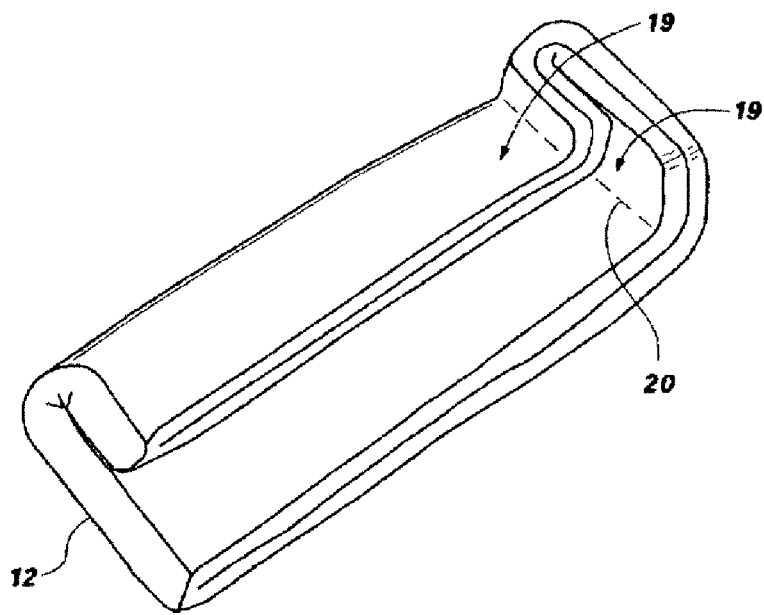
FIG. 3C is a perspective view of the diaper of FIG. 3B in the process of folding the diaper along a crosswise aspect of the diaper.
Figure 3D:
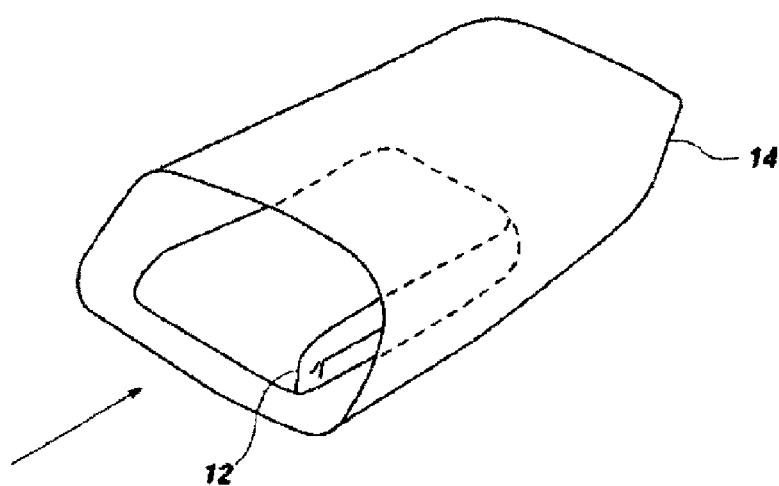
FIG. 3D is a perspective view of the diaper of FIG. 3C being disposed within an encasement.
Figure 3E:
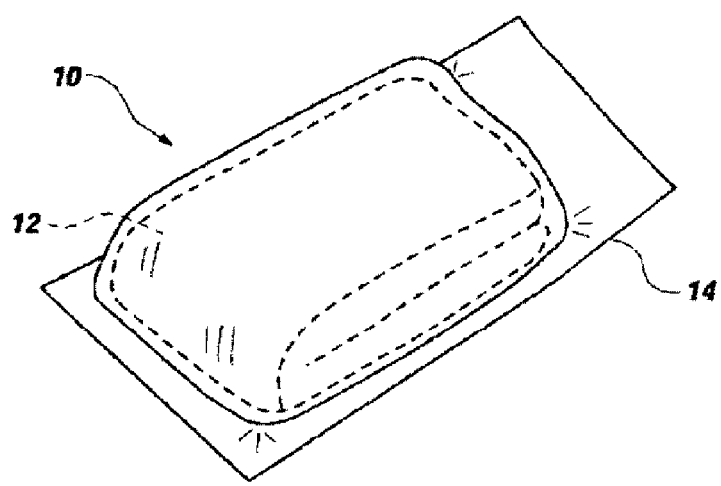
FIG. 3E is a perspective view of the diaper of FIG. 3D held under vacuum within the encasement of FIG. 3D.

Shown in series in FIGS. 3A through 3E is one aspect of the invention in which a diaper is reduced from its nominal volume or size to a reduced volume or size. Diaper 12 begins with a nominal volumetric configuration, sized and shaped as may be conventionally provided by a manufacturer of the diaper. In this embodiment, the diaper is reduced in volume by fold 17 along a lengthwise aspect of the diaper, shown at line 18. In FIG. 3C, the diaper 12 is folded at 19 along a crosswise aspect of the diaper, shown at line 20. Progressing to FIG. 3D, once the diaper has been folded a desired number of times; the folded diaper is disposed within encasement 14, which is formed of a substantially air impermeable material. Encasement 14 can then be evacuated to form a relative vacuum within the encasement, after which the encasement can be sealed to maintain the vacuum in the diaper and the encasement.

It will be understood by those skilled in the art that the process of forming a vacuum within the diaper and the encasement will extract at least a portion of air contained within the diaper. By removing a majority of excess air from the diaper, the diaper can be compressed upon itself by atmospheric pressure and consume a reduced amount of space corresponding to the amount and volume of air removed from the diaper.

In addition to the process illustrated in FIGS. 3A through 3E, in another aspect of the invention, a method of packaging a diaper is provided and includes the steps of volumetrically reducing a size of the diaper to a size convenient for carriage and storage of the diaper. The volumetrically reduced diaper can then be disposed within an encasement. The volumetrically reduced, convenient size of the diaper can be maintained by a pressure differential acting upon the encasement. As used herein, the term "convenient size" is understood to refer to a size and configuration of a diaper that can be easily and conveniently stored in a pocket, handbag, purse, etc., and consume very little space within the pocket, handbag, etc. Such a size will be appreciated to be essentially a "pelletized" or "capsulated" or "pocket sized" or "pocketable" (as defined above) version of the diaper, having bulk due to air spaces removed, and will be generally cylindrical, rectangular, etc, and can have rounded or square corners. Generally, the largest dimension will be about four inches or less. However, for certain specialized applications such as kits contained in a feeding bottle, a longer, more "sticklike" shape may be used in one embodiment. But likewise a cylindrical or square configuration having height, width, and length dimensions of roughly equal magnitude can also be advantageous in such a kit in another embodiment. The salient point is that the size is convenient to carry and conceal.

The size of the diaper can be volumetrically reduced in a number of manners, including pressing the diaper into a mold or other cavity. In this example, the encasement in which the diaper is disposed can be sized and shaped to correspond closely to the volumetrically reduced size of the diaper. Once disposed within the encasement, the force applied to compress the diaper into the mold can be released, after which the diaper will tend to return to its nominal size and shape, but will be restrained by the encasement. The pressure differential acting upon the easement will thus be the result of the diaper tending to expand into its nominal configuration. An equilibrium will be reached between a) the restoring force tending to expand the diaper; and b) a combination of the hoop strength (resistance to expansion of the encasement via deformation of the encasement) and the pressure differential tending to compress the diaper. Depending on the material from which the encasement is made, this can be made to be predominantly hoop strength or predominantly air pressure differential.

Figure 4:
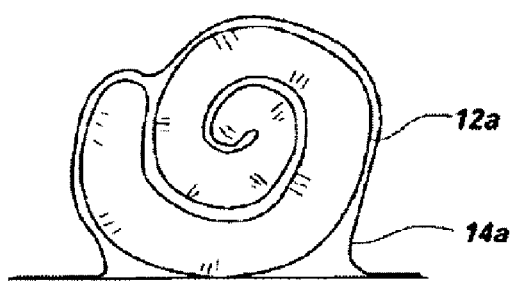
FIG. 4 is an end view of a packaged diaper having a reduced volume in a substantially cylindrical shape in accordance with one aspect of the invention.

While the example packaged diaper shown in many of the figures of this disclosure includes a generally rectangular shape, it is contemplated that the volumetrically reduced diaper can be of a variety of sizes and shapes. For instance, as shown in FIG. 4, volumetrically reduced diaper 12a can have a substantially cylindrical shape. This embodiment may be beneficial, for example, in applications in which the diaper is to be stored in rounded or cylindrical receptacles, such as cans or tubes. As will be appreciated, by forming encasement 14a from a flexible, substantially air impermeable material, a vacuum formed within the encasement will force the encasement to conform to the general shape of the reduced volume diaper. In this manner, the diaper can be formed in a variety of reduced volume shapes for a variety of applications.

In another example embodiment the encasement shape can control the shape of the packaged diaper. For example, a diaper can be compressed into an encasement within a mold cavity which encasement has a shape which essentially follows the shape of the mold. Thereafter the encasement maintains that shape, though the diaper may expand slightly against the hoop strength, air pressure differential, or combination thereof.

Figure 5:
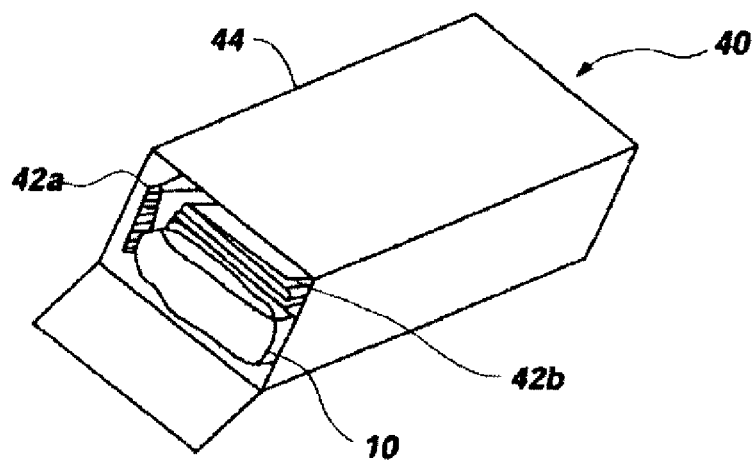
FIG. 5 is a perspective view of a diaper kit in accordance with one aspect of the invention.

As illustrated in FIG. 5, in another aspect of the present invention a diaper kit 40 is provided. The kit can include a packaged diaper 10 in accordance with the embodiments discussed above and at least one diaper accessory 42. A container 44 is also provided, in which each of the packaged diaper and the diaper accessory are disposed. The diaper accessory can be a variety of items, including, but not limited to, a diaper rash ointment or other medicament, talcum powder/baby powder, a lotion, moist or dry wipes, cotton swabs, dirty diaper disposal bag, etc., as may be needed in caring for an infant or incontinent person, as will be known to one skilled in the art of providing products for care of such persons. In the example embodiment shown, a packet of ointment 42A is included in the kit, as are moist wipes 42B.

Thus, in one example, substantially all of the materials necessary for changing a soiled diaper are provided in a small, space optimized kit that can be easily carried or stored by a caretaker of an individual requiring diapers. The kit can be advantageously used as a daily staple of caretakers, or may be used in specialized circumstances such as outdoor activities, travel, or business or recreational events away from home, or other situations in which space and convenience of carriage may be of a premium. In such circumstances the caretaker may wish to minimize the number of articles needing carriage, and can advantageously carry one or two kits, as may be needed, and dispense with the conventional diaper bag that would otherwise have to be carried during the event or activity. Also, the reduced size of the present diaper kit can allow one or more kits to be stored in an out-of-the-way location, such as a glove box of a car, and retrieved in "emergency" situations in which spare diapers were forgotten or consumed.

In another embodiment, the kit can be configured for use by an incontinent adolescent or adult. The kit can further include supplies to touchup stains on clothing. It can contain a small container of perfume or cologne, a small container of odor reducing spray, or other items which an incontinent adult may find needful and reassuring to carry, in addition to supplies which customarily may be needed to change a diaper, including a clean diaper, wipes, and lotion, ointment or other medicament, to name some examples.

Figure 6:
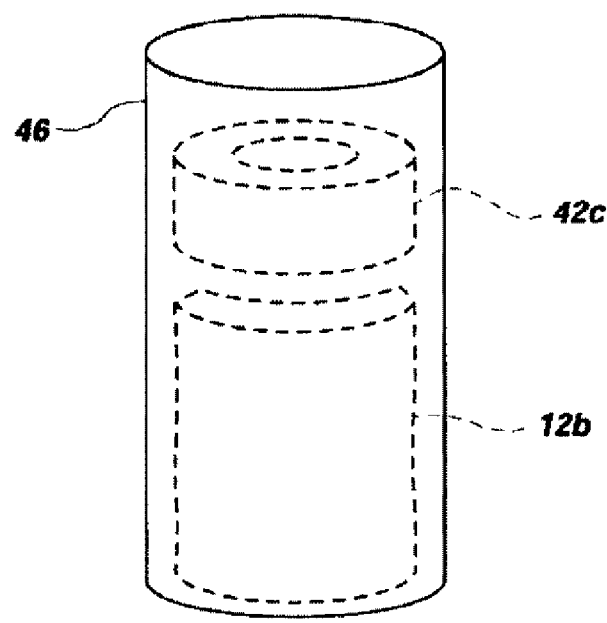
FIG. 6 is a perspective view of another diaper kit in accordance with one aspect of the invention.
Figure 6A:
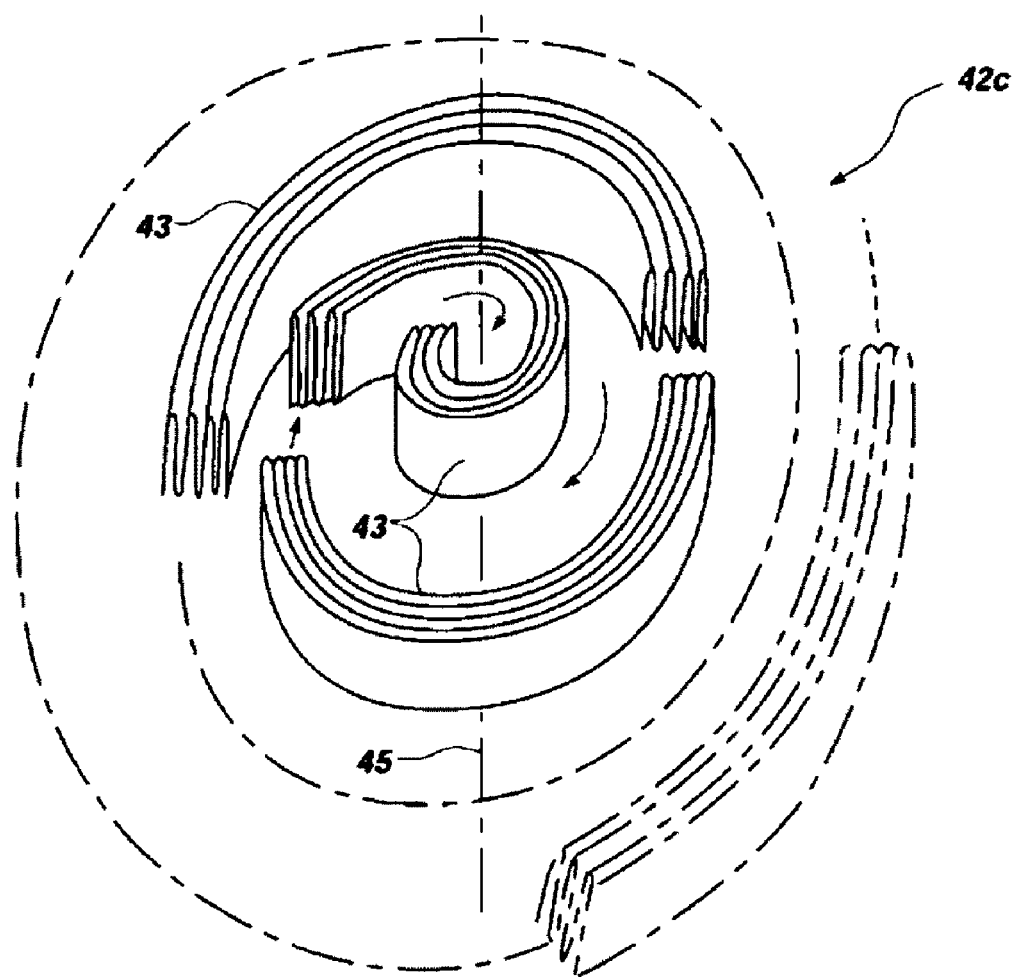
FIG. 6A is a perspective view of a diaper wipe configuration usable with the kit of FIG. 6 in one example in accordance with one aspect of the invention.

As shown in FIG. 5, the diaper kit 40 can include a container 44 that is substantially rectangular in shape. Such kits can be easily stacked and stored and will fit neatly into a pocket, purse or other baggage. In another embodiment, as shown in FIG. 6, the container 46 can be substantially cylindrical in shape. In this embodiment, the diaper 12b can be formed in a cylindrical shape, or other shape to facilitate maximum use of available space within the cylindrical container. Also included in the illustrated example shown in FIG. 6 are moist wipes 42C which can be arranged in a disk-like or toroidal configuration for disposal within the cylindrical container. With reference to FIG. 6A, the individual wipes 43 are accordion folded, then rolled about an axis 45 transverse to the folds. A surprisingly large number of wipes thus configured can be fit into a surprisingly small space. In this manner, 6 or 7 wipes or another selected number of wipes can be stored within the container 46 to ensure ample supply.

Figure 7:
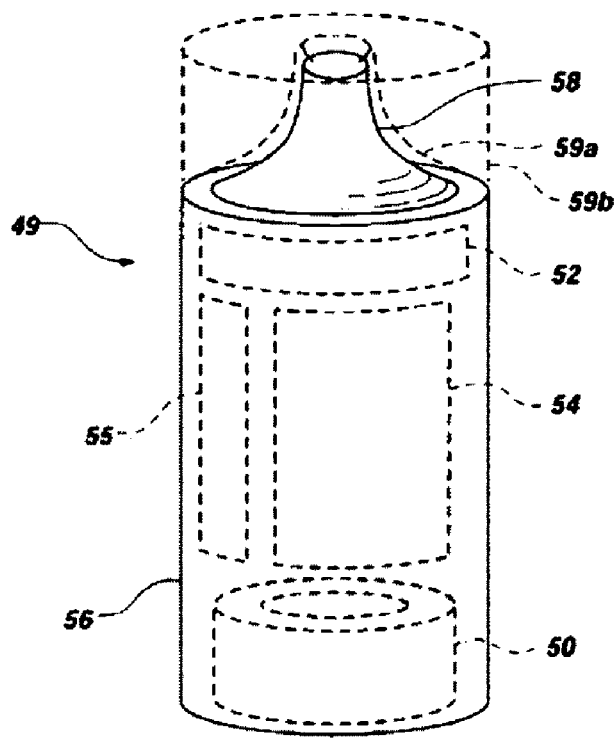
FIG. 7 is a perspective view of an infant care kit in accordance with one aspect of the invention.

In another aspect of the invention, illustrated by example in FIG. 7, an infant care kit 49 can be provided which includes a diaper 50, one or more diaper accessories 52 and a portion of infant food 54. An infant feeding bottle assembly is also provided having a hollow body 56 and a nipple food delivery portion 58 of the device couplable thereto. A cover 59a or 59b can be provided, which keeps the feeder portion sanitary. This can be a throwaway tear-off film cover (e.g. 59b) or a more conventional replaceable cap (e.g. 59a). The feeding apparatus can be single use (i.e., disposable) or reusable. As shown, the diaper, diaper accessory, and portion of infant food can be disposed within the infant feeding assembly for convenient carriage. The infant feeding assembly can thus be configured to: i) contain each of the diaper, diaper accessory and portion of infant food; and ii) upon removal of the diaper and diaper accessory, receive the portion of infant food (and water, if applicable) within the hollow body and thereby enable delivery of the infant food to an infant via a food delivery device erstwhile acting as a container for the kit. In one embodiment the nipple portion can be configured for delivery of baby formula, and in another embodiment it can be configured for delivery of a flowable baby food such as a formula/cereal mixture, creamed vegetables or fruit, or the like. In one embodiment the baby food can be in powder form, reconstituted by addition of water. A chemical warming pack (similar to or the same as a conventional hand warming pack) can be provided for use in warming the baby formula or other baby food.

In this example implementation, substantially all of the materials necessary to feed and change a diaper of an infant are provided in a compact, easily carried kit. A caretaker of the infant can use the kit to store the provided items, and when desiring to feed the infant, can prepare the portion of infant food and feed the infant with the infant feeding assembly, shown in this embodiment as similar to a conventional baby bottle, but provided with a detachable bottom.

As shown in the illustrated example, the hollow body 56 of the feeding assembly 49 can be substantially cylindrical in shape, although other shapes are also contemplated, such as squared, triangular, and other polyhedral cross-sectional shapes. The portion of infant food can include a variety of foods suitable for consumption by infants, including powdered baby formula and condensed baby formula, freeze dried, powdered, concentrated creamed vegetables and fruits and other baby foods, as well as cereal mixes, etc. A caretaker can easily remove all items from the feeding assembly, configure it for feeding, and returning the portion of infant food (with water, as mentioned, if necessary, or other fluid which can be added to the infant food) and the food can be fed to the infant via a food delivery device 58, a conventional baby bottle nipple in the illustrated embodiment.

In one embodiment, the feeding apparatus can include a double wall configuration to provide increased insulation so as to keep formula or other baby food at a desired temperature for a longer period of time. To facilitate this, or, to provide initial warming when hot potable water is unavailable, a heat source 55, as mentioned, can also be disposed within the feeding assembly. The heat source can be configured to provide heat for warming the portion of infant food, as well as any fluid having been added to the infant food. In situations where it may be necessary to add cold fluid such as milk or water to the infant food, the fluid and food can be warmed to a temperature well tolerated and more acceptable to an infant. As mentioned, the heat source can be a conventional chemical heating apparatus, such as those producing an exothermic reaction when two or more separate materials are mixed, or are exposed to air. These can be packets of reactants in granular form, chemically activated gel heating sources, etc. The feeding apparatus can be configured to cooperate with the heat source to heat the baby formula or other food. In one embodiment, the kit can include an outer container (not shown) which is the outer wall of the double wall configuration mentioned. This can be a continuous wall, or can comprise vents (e.g. to expose air to air-reactant heating pads). A mesh or other textile can be used as the material forming the outer containment in which the infant feeding assembly is disposed. The outer container can be configured to receive and protect the feeding assembly and can also encompass the heating source to maintain close contact between the heating source and the hollow body 56.

In another embodiment, the heat source can be some other means of providing heat, for example provision of a metal outer sleeve, annular space for water, and inner container for formula or food enabling use of a cigarette lighter, a solar reflector or magnifier, or some other higher temperature heat source to heat the outer sleeve and still enable more gentle warming of the contents of the inner sleeve. Such an arrangement would also facilitate rapid cooling of the outer sleeve after removing the high temperature heat source so that it can be safely handled, enabling removal of the inner sleeve for feeding for example.

Figure 8:
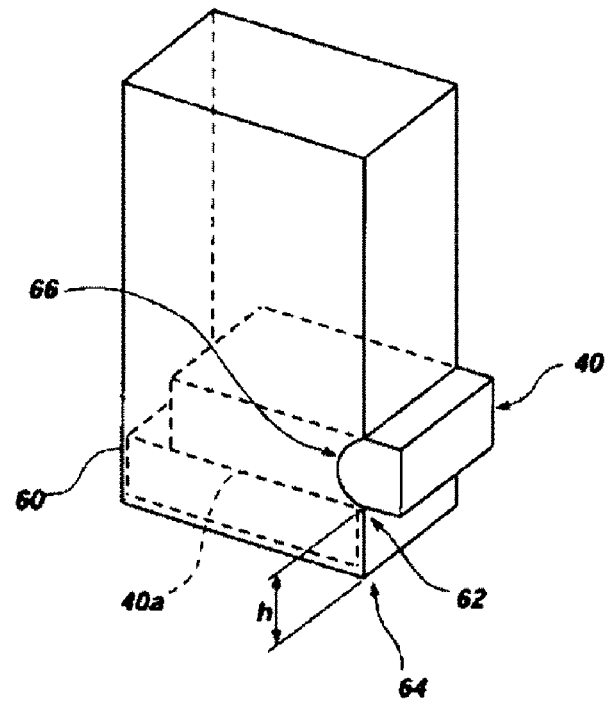
FIG. 8 is a perspective view of a master container in accordance with one aspect of the invention.

In another example embodiment of the invention, shown in FIG. 8, a plurality of single use packaged diapers (not shown), or diaper kits 40, 40A can be provided packaged together, each stacked vertically in a master container 60. The master container 60 can include a removable access panel (previously removed in FIG. 8) through which one 40 of the plurality of containers can be accessed. Providing for the removable access panel can be in one of a variety of ways known to those in the art, including a perforated removable panel or hinged panel. A bottom 62 of the access panel can be disposed in the master container 60 in a location vertically displaced from a bottom 64 of the master container by a distance substantially equal to a height "h" of the container. It has been found that having the last container to be used positioned below the access panel helps keep the shape of the master container and improves appearance over the dispensing life of the product.

In this manner, as a kit is removed from the master container, the kit immediately above the removed kit will fall into place to be easily removable from the master container. Notches 66 can be provided adjacent the removable panel to enable easy withdrawal of kits through the panel. The master container 60 can be used to package and ship a number of kits 40, and advantageously also used to dispense the kits at a retail center or other point of sale. While the master container shown in FIG. 7 is configured to store and dispense 6 diaper kits, master containers configured to store and dispense fewer or more kits can also be provided, and include two or more access panels disposed and oriented in a variety of locations on the master container.

Figure 9A:
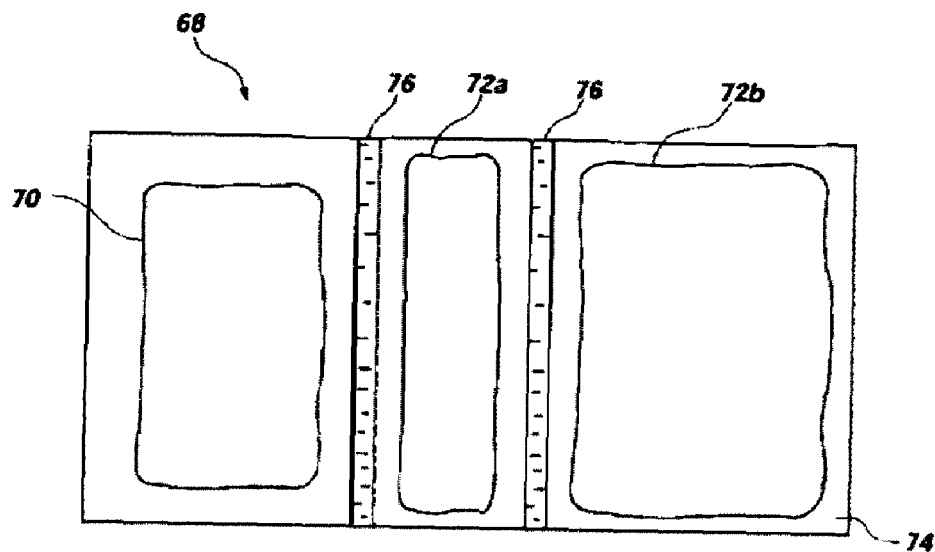
FIG. 9A is a top view of another diaper kit in accordance with one aspect of the invention.
Figure 9B:
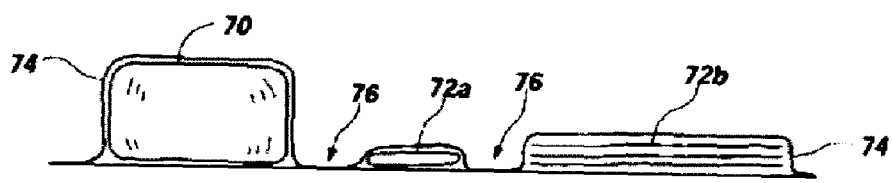
FIG. 9B is a side view of the diaper kit of FIG. 9A.

Illustrated in FIGS. 9A and 9B is a diaper kit 68 in accordance with another example implementation of the invention. In this embodiment, a diaper 70 and various diaper accessories 72 are contained within an encasement 74. The accessories can include baby ointment, baby wipes, powder, etc. as discussed above. In this example the accessories include baby ointment 72A and wipes 72B. Other accessories can be substituted or additionally included. Shown at 76 are seams formed in the encasement defining adjacent compartments that can each hold a different product. The seams can separate products to enable differing treatment of the products in relation to the encasement. For instance, diaper 70 can be disposed in the encasement in a reduced volumetric configuration, as discussed above, and the encasement can be evacuated and vacuum-sealed about the diaper. However, the baby ointment 72A can be vacuum sealed (if already packaged in an impermeable containment without excess air) but need not be vacuum sealed (indeed it may be difficult to do so if not already packaged) in its corresponding compartment. Likewise the wipes 72*b* are not vacuum packed, but could be if previously enclosed in an impermeable containment without excess air.

While it may be desirable to vacuum-pack the diaper 70, and it is possible to do so with some accessories, it may be the case that certain accessories are not well suited to such an arrangement. For instance, with regard to the previously mentioned examples of ointment 72*a* and wipes 72 not pre-packaged, baby wipes are often saturated or at least moisture-laden with a liquid cleaning compound similar in appearance to soapy water, to aid in the cleaning process associated with changing diapers. When subjected to a vacuum, the moisture may be withdrawn from the wipes, leading to poor performance of the wipes. In addition, if undue moisture is removed during the vacuum process, the moisture may interfere with sealing the encasement once vacuum has been drawn, leading to premature breach of the encasement. The same applies to the ointment, it would be likewise problematic to vacuum pack it, even more so. Thus, for some products a vacuum seal may not be desirable or necessary, and those products can be sealed in the encasement without being placed under vacuum.

To address these issues, the present invention in one embodiment advantageously provides a diaper kit that can include differently and variably treated compartments. In the example shown, the compartment containing the diaper 70 can be treated with a vacuum to aid in maintaining the volumetrically reduced configuration of the diaper. The compartment holding the ointment 72A may or may not be vacuum treated, as the situation dictates. The compartment holding the wipes 72B can be simply sealed to retain the moisture in the wipes without drawing any moisture out with a vacuum process. Other compartments (not shown) can be treated according to the product stored in each one.

Figure 9C:
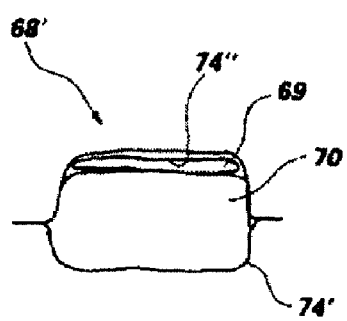
FIG. 9C is a side view of another example diaper kit in accordance with one aspect of the invention.

In addition to the compartmentalized encasement shown in FIGS. 9A and 9B, it is contemplated that in another example embodiment of the invention, shown in FIG. 9C, one can provide a diaper kit 68' in which all of the components of the kit are contained in an encasement 74' and sealed under vacuum. For example, the diaper wipes 69 and/or other accessories can be pre-packaged in one or more casings 74" with liquid and wipe material therein. In this way, both a diaper and one or more accessories, together forming a single use kit, can be integrally packaged in one encasement 71', and can all be accessed once the encasement has been breached.

Figure 10A:
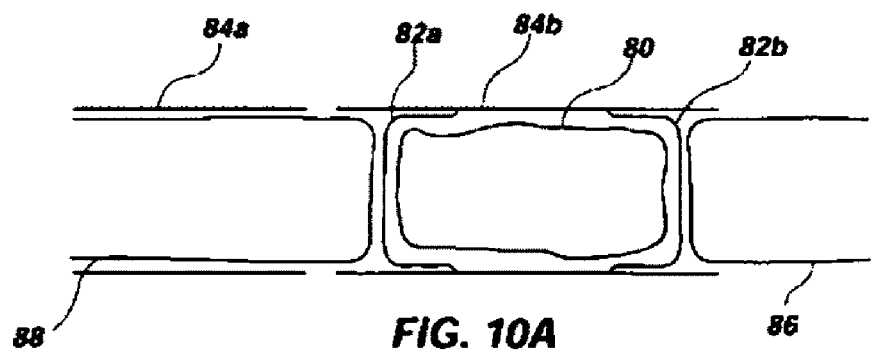
FIG. 10A is a schematic view of one step of a process of packaging a diaper in accordance with one aspect of the invention.
Figure 10B:
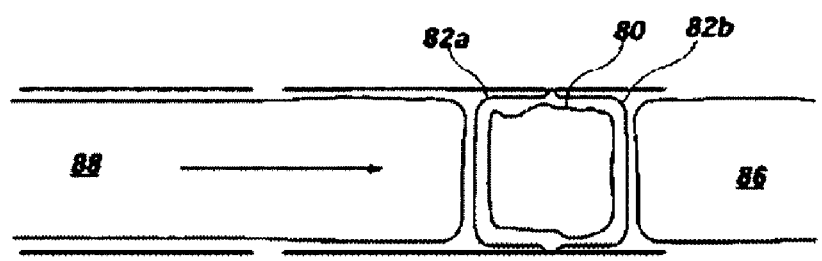
FIG. 10B is a schematic view of another step of the process of FIG. 10A.
Figure 10C:
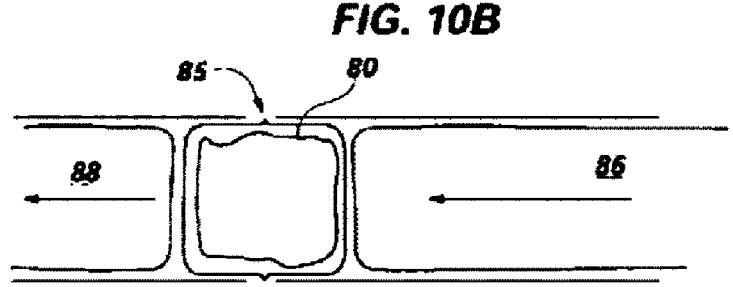
FIG. 10C is a schematic view of another step of the process of FIG. 10A.
Figure 10D:
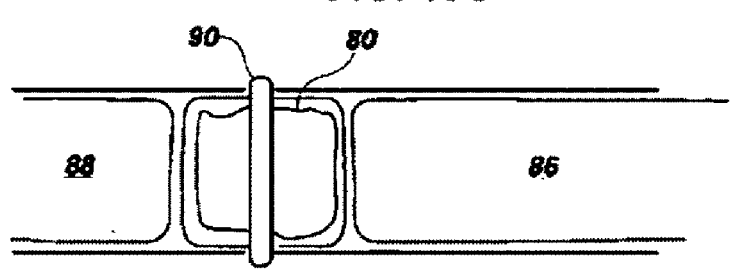
FIG. 10D is a schematic view of another step of the process of FIG. 10A.

With reference to FIGS. 10A through 10E, in one embodiment of the invention the encasement in which the volumetrically reduced diaper is disposed can contain the diaper without any substantial pressure differential acting upon the encasement. One illustrative process in which this can be achieved is illustrated in FIGS. 10A through 10E. In this embodiment, a "loose" diaper 80 is placed within a chamber 84B with a pair of encasement shells 82 disposed adjacent ends of the diaper. Rams 86 and 88 can be activated to compress the diaper into a volumetrically reduced configuration, as illustrated in FIG. 10B. Once optimal reduced volume is achieved, the diaper/shell assembly can be moved adjacent a channel 85 defined between the chambers 84A and 84B, as illustrated in FIG. 10C.

Figure 10E:
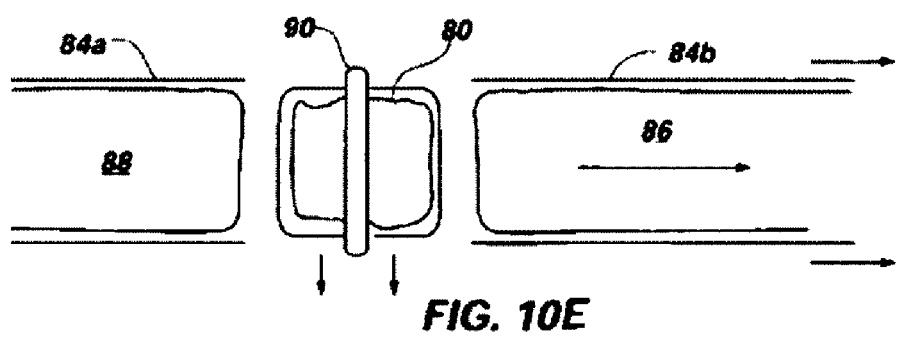
FIG. 10E is a schematic view of another step of the process of FIG. 10A.

Channel 85 can provide access to the diaper/shell assembly to enable attachment of a clamping strap 90 to the shells 82. The strap can aid in maintaining relative position of the shells 82 after the pressure applied to reduce the volume of the diaper is released. Thus, as shown in FIG. 10E, the rams 86, 88 and chambers 84 can be removed from contact with the diaper, and the encasement maintains the diaper/shell assembly in the volumetrically reduced configuration. In this manner, it is not necessary to apply a vacuum to the encasement to create and maintain the volumetrically reduced size of the diaper. In another embodiment, the encasement can be made air tight by application of the clamping strap, and thus a combination of differential pressure and hoop strength of the encasement can contain the diaper after the encasement expands to an equilibrium state.

Figure 11A:
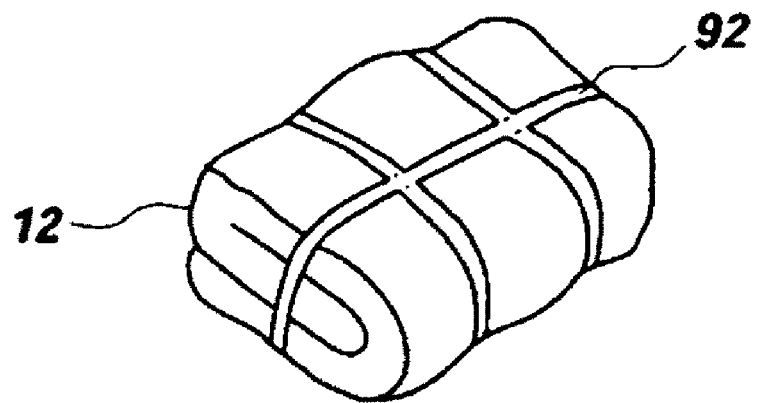
FIG. 11A is a perspective view of a diaper held by a restraint in accordance with one aspect of the invention.
Figure 11B:
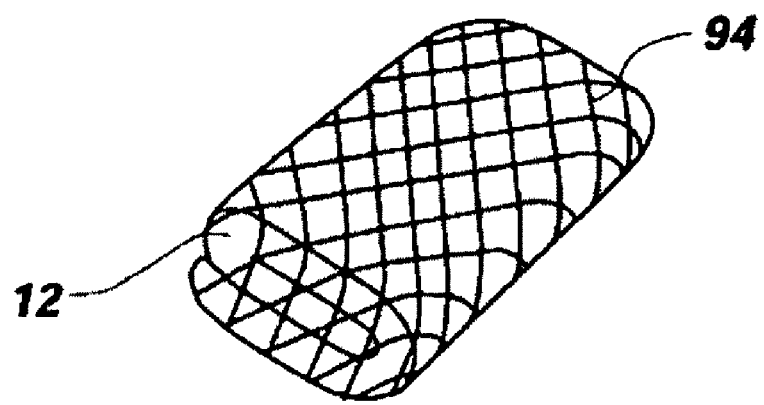
FIG. 11B is a perspective view of a diaper held by another restraint in accordance with one aspect of the invention.

As shown in FIGS. 11A and 11B, in one aspect of the invention, a restraint 92 can be provided in which the diaper 12 can be disposed a second, reduced size, relative to a first, nominal size. The restraint 92 can confine the diaper so that the diaper is retained in its reduced size by the restraint and so that the diaper is returned to its nominal size upon opening of the restraint. The restraint can be a strap or a series of independent or interconnected straps, or, as shown in FIG. 11B, the restraint 94 can include a webbed material. The restraint can be formed of a material having sufficient strength to retain the diaper 12 in the reduced size, but can be removed by a consumer to release the diaper into the first, nominal size, for example by exploiting an engineered weakness, as is conventionally provided in "tear-away" packaging closures.

Figure 12:
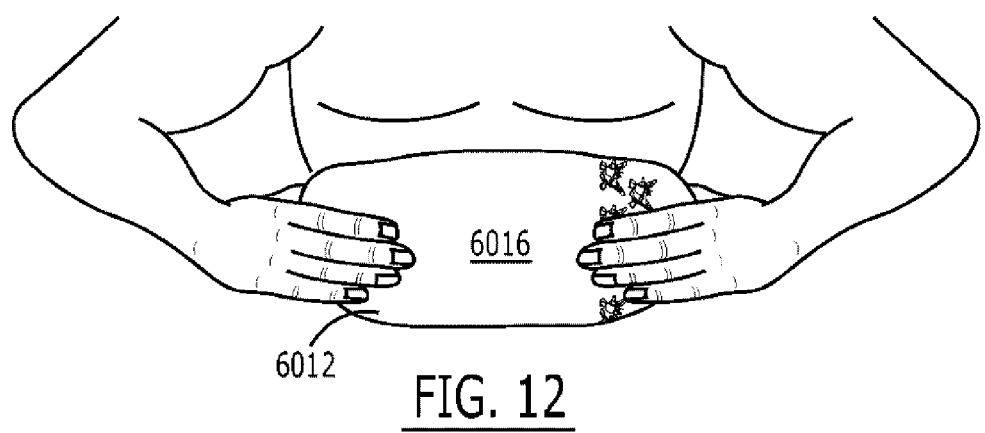
FIG. 12 is a view of a bulky diaper in the hands of a person.
Figure 13:
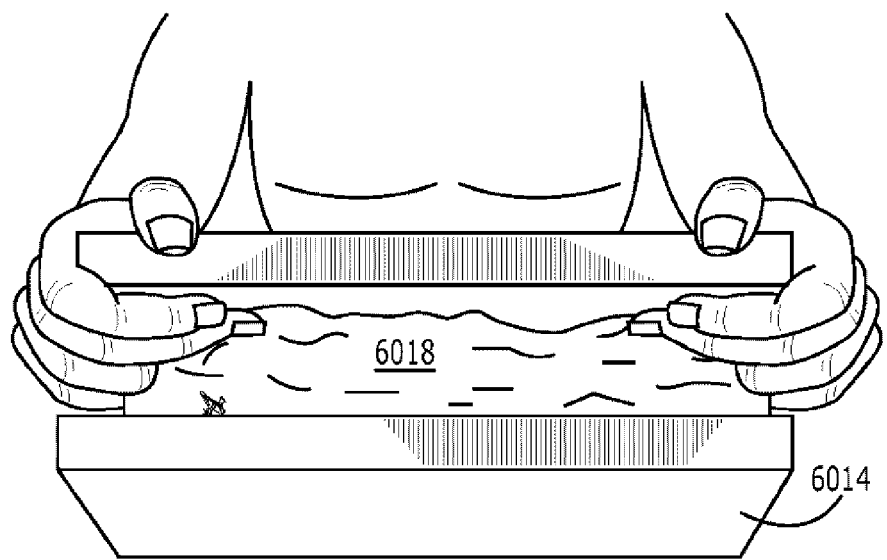
FIG. 13 is a sketch of a diaper within a jig made for holding and folding said diaper, with a person tucking the rough edges inwardly.

An embodiment of a method for packaging a diaper very compactly by folding and vacuum-sealing is shown in FIGS. 12–19. First, a bulky diaper 6012 as shown in FIG. 12 is inserted into a U-shaped elongated open-ended forming jig 6014 as shown in FIG. 13 with the outside 6016 of diaper facing down into the jig and the inside 6018 of the diaper facing up and out of the jig. The ragged elastic banded edges of the diaper are tucked inward so as to obtain a smooth clean line exterior.

Figure 14:
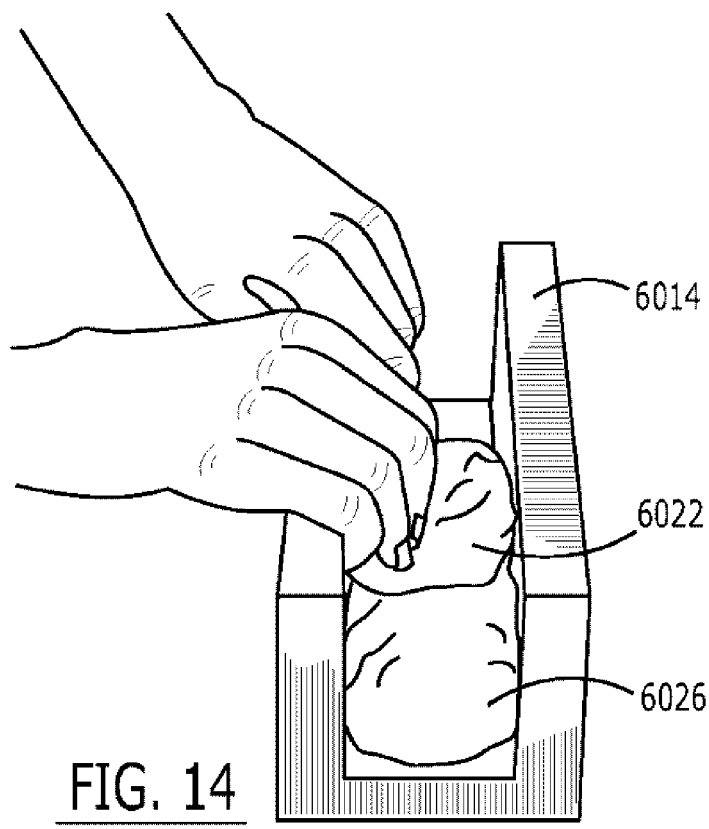
FIG. 14 is a view of a diaper with one end being folded inward.
Figure 15:
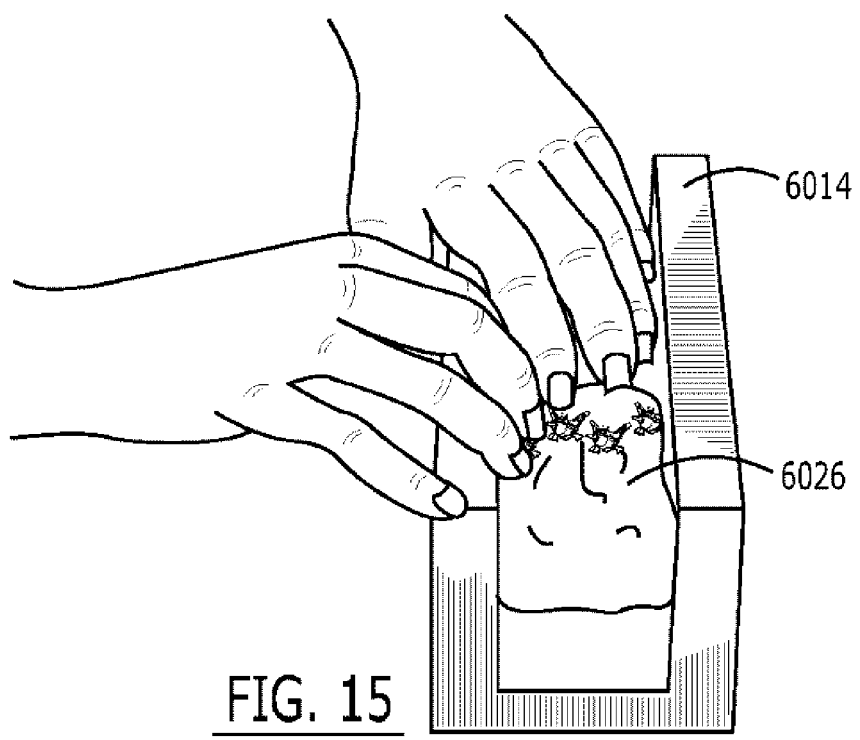
FIG. 15 is a view of a diaper with the other end being folded inward over the first fold.

Thereafter, as shown in FIG. 14, a first end, such as end 6022, then is folded inwardly covering a middle portion of the diaper, and then the other end 6026 is folded in over the first end 6022 and middle portion to form a rectangular shape of the diaper as shown in FIG. 15.

Figure 16:
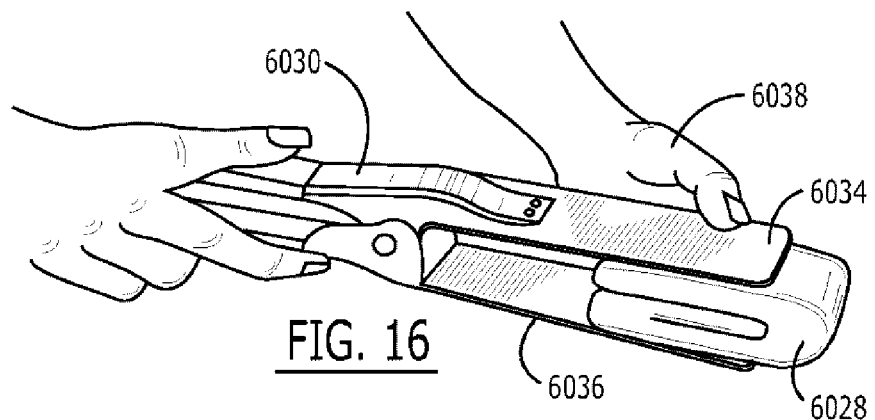
FIG. 16 shows a hand clamp gripping a folded diaper.

A spring-tensioned hand-clamp 6030 then is opened to receive the completely folded diaper between an upper flat rectangular jaw 6034 and a lower jaw 6036, as shown in FIG. 16. Furthermore, the clamp 6030 and a hand 6038 each compress the diaper 6028 as shown in FIG. 16.

Figure 17:
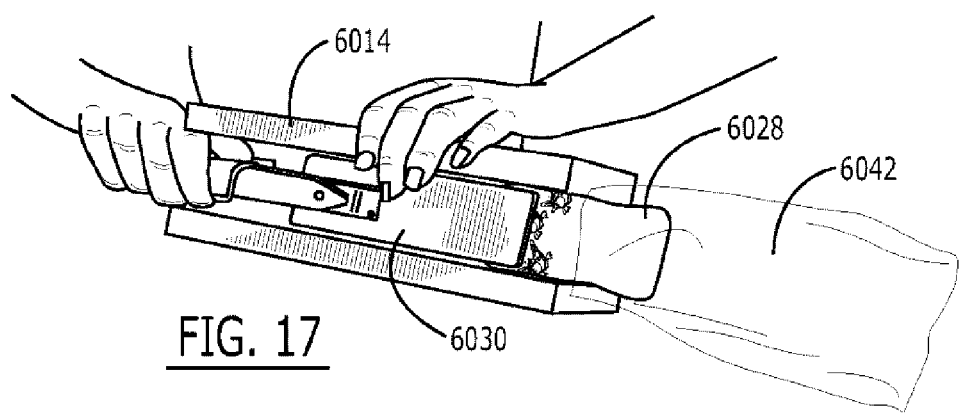
FIG. 17 is a perspective view of a folding jig facilitating the hand clamp for inserting a diaper into a plastic bag.
Figure 18:
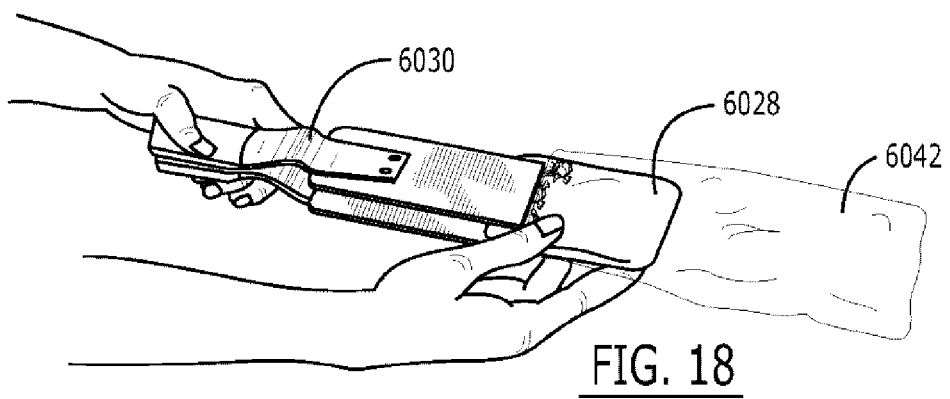
FIG. 18 shows a hand clamp held by a person compressing a folded diaper being inserted into a plastic bag.
Figure 19:
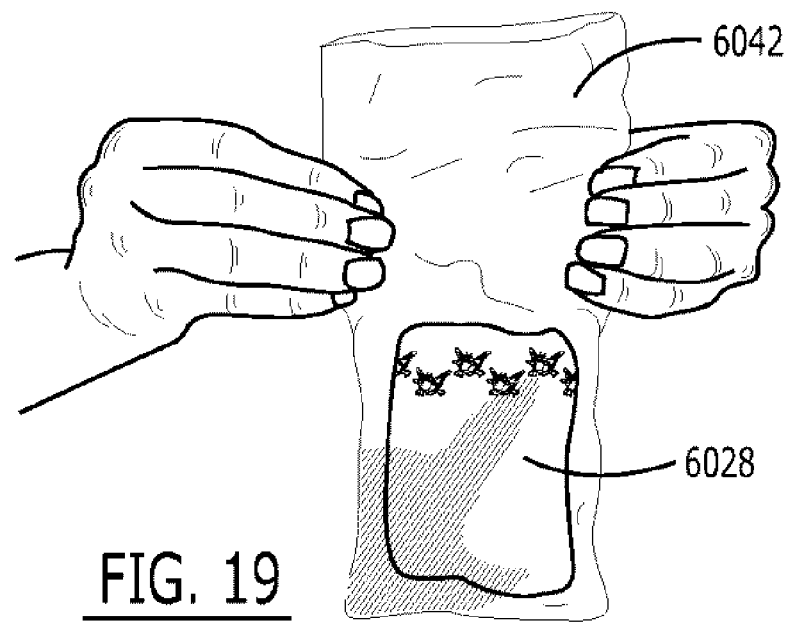
FIG. 19 shows a folded and compressed diaper within a small plastic bag.

The compressed, folded diaper 6028 then is inserted into an open end of a pliable, resilient bag 6042. The diaper is inserted into the bag using the hand clamp 6030 and jig 6014 to facilitate the insertion as shown in FIG. 17, or, alternatively, as shown in FIG. 18, the compressed, folded diaper 6028 is directly inserted into the open-ended bag 6042 without the jig.

The folded diaper 6028, fully inserted into the bag 6042 (FIG. 19), is then placed onto the deck of a conventional vacuum-sealing machine, such as a vacuum sealing-machine sold under the trademark SUPERVAC. The lid of the machine is fastened down and the vacuum-sealing machine vacuum-seals and cuts the bag to form a finished product as shown in FIG. 20.

The finished product is very firm and dense, looks like a taffy candy bar, and is comparable in size to a candy bar. In one embodiment, the finished product, i.e., a vacuum-sealed diaper package, measures approximately 1 inch by 2 inches by 1½ inches, and fits into a box for convenient carrying within a purse.

Figure 20:
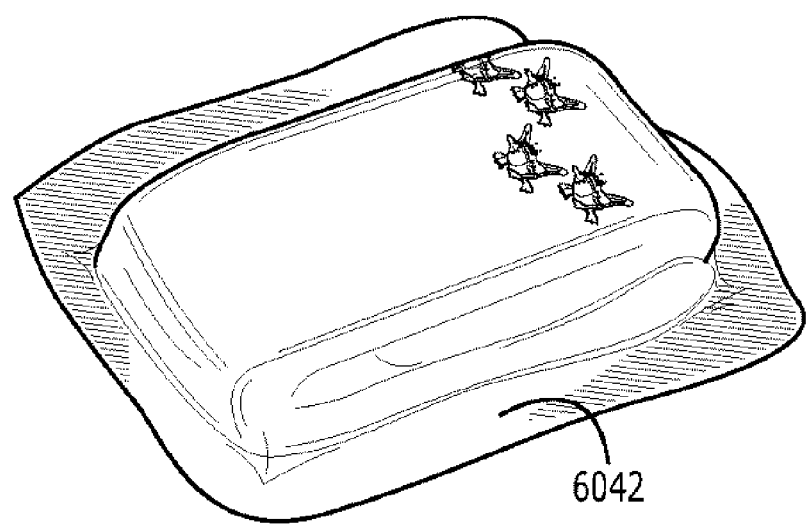
FIG. 20 shows a folded, compressed, and vacuum-packed diaper within the plastic bag of FIG. 19 after vacuum-sealing.

Additionally, printing on the outside of the diaper is visible through the bag 6042 as shown, for example, in FIG. 20. Alternatively, the printing on the outside of the diaper may be disposed within the folded diaper by first folding end 6026 inwardly covering a middle portion of the diaper and then folding the end 6022 in over the end 6026 and middle portion to form the rectangular shape of the diaper.

Figure 21A:
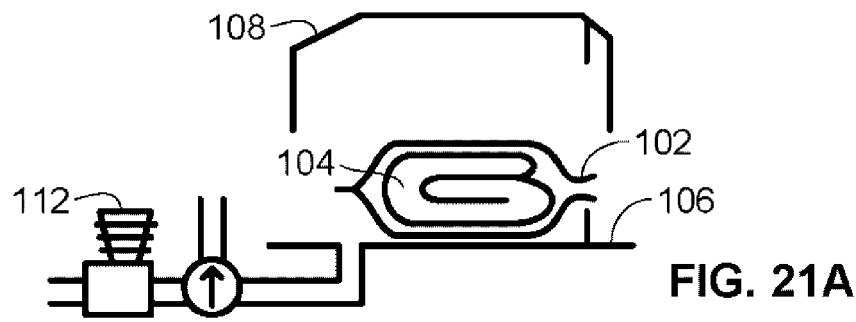
FIG. 21A is a schematic view of one step of a method of packaging a diaper.
Figure 21B:
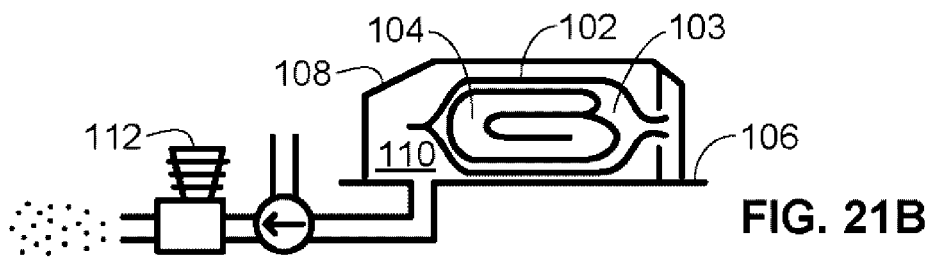
FIG. 21B is a schematic view of another step of the method of FIG. 10A.
Figure 21C:
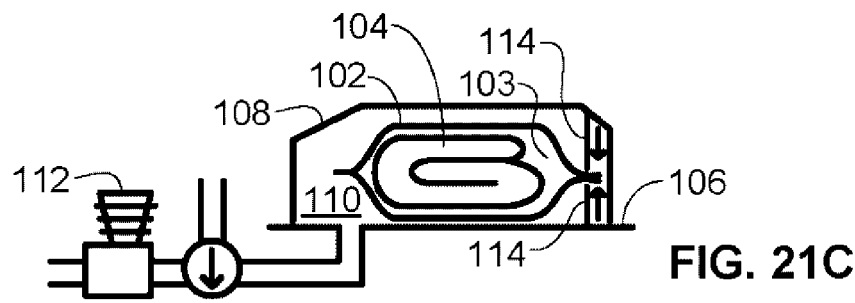
FIG. 21C is a schematic view of another step of the method of FIG. 10A.
Figure 21D:
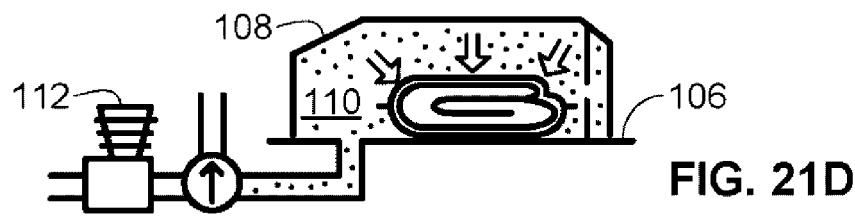
FIG. 21D is a schematic view of another step of the method of FIG. 10A.
Figure 21E:
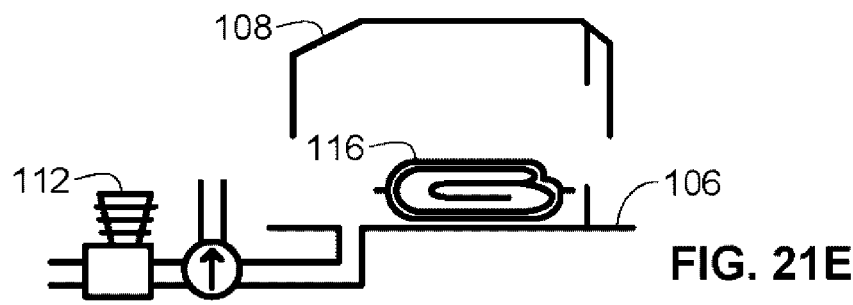
FIG. 21E is a schematic view of another step of the method of FIG. 10A.

One or more embodiments of the invention relate to a method of packaging a diaper using a conventional vacuum-sealing machine. As shown in FIG. 21A, a compressible absorbent diaper 104 is disposed within a flexible substantially air impermeable encasement 102 and the unsealed encasement 102 with the diaper 104 therein is then placed onto the deck 106 of the vacuum-sealing machine. The lid 108 of the machine is then lowered as shown in FIG. 21B establishing a seal with the deck to define a chamber 110 with the unsealed encased diaper within the chamber. A pumping system 112 then evacuates ambient air from the chamber 110 creating a vacuum state within the chamber and within the interior space 103 defined by the encasement with the diaper 104 therein. Sealing bars 114 then seal the encasement as shown in FIG. 21C such that the interior space of the substantially air impermeable encasement 102 is completely sealed and such that the compressible absorbent diaper 104 is completely enclosed within the sealed interior space 103. As shown in FIG. 21D, ambient air pressure is then restored to the chamber effecting a pressure differential across the sealed encasement that acts upon the encasement to compress the compressible absorbent diaper 104 and maintains the diaper in a reduced volume (FIG. 21D) that is less than the volume of the diaper at the time the encasement was sealed (FIG. 21C, before ambient air pressure was restored to the chamber). As shown in FIG. 21E, the lid 108 is then raised and the vacuum-packed diaper 116 is available for removal from the machine.

In addition to the above disclosure, another aspect of the invention relates to vending and, in particular, to vending systems and machines for dispensing volumetrically reduced absorbent articles such as vacuum-packed diapers. Indeed, it may be particularly beneficial to include such a vending machine in conjunction with each courtesy baby changing station commonly found in public restrooms of commercial establishments.

Figure 22:
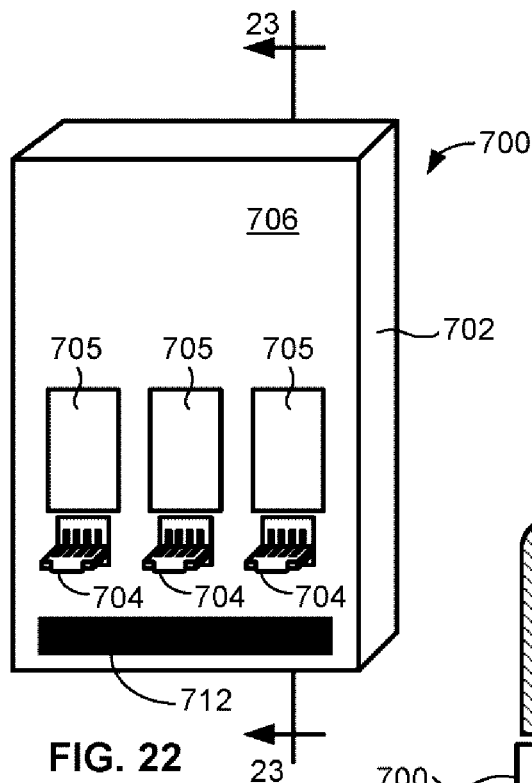
FIG. 22 is an illustration of a vending machine in accordance with the invention.
Figure 23:
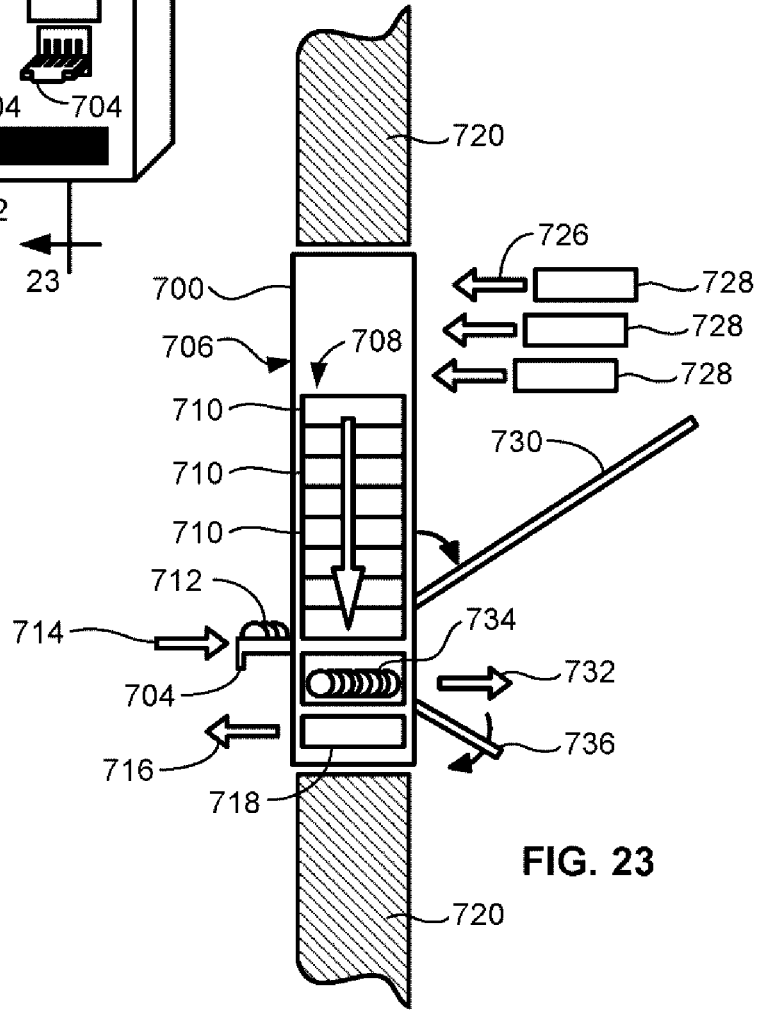
FIG. 23 is cross-sectional illustration of the vending machine of FIG. 22 taken along the line 23—23 in FIG. 22.

An exemplary vending machine 700 is shown in FIGS. 22–23. Vending machine 700 includes a structural housing 702 and multiple, slotted, currency-receiving slides 704 extending from an anterior vending face 706 of the vending machine 700. The vending machine 700 further includes viewing windows 705 for presentation of selectable products that are respectively dispensed upon actuation of the currency-receiving slides 704. Each product is dispensed for a predetermined currency amount that is optionally indicated in the respective viewing window 705 or on the respective currency-receiving slide 704.

As shown in FIG. 23, the exemplary vending machine 700 contains, in association with each currency-receiving slide, a vertical stack 708 of products 710. In selecting and purchasing a product, a consumer places currency 712 into a particular currency-receiving slide 704, actuates the slide by pressing the slide inwardly in the direction of arrow 714, and receives 716 one of the selected products 718 associated with the particular currency-receiving slide 704 through dispensing slot 712 (FIG. 22).

As further shown in FIG. 23, the exemplary vending machine 700 preferably comprises posterior access panels for secure access by a vendor or operator of the vending machine 700. In this respect, the vending machine 700 extends through a wall 720 (FIG. 23) in which it is mounted. Consequently, a vendor may securely restock (726) the vertical stack 708 with additional products 728 through a product access panel 730. Furthermore, a vendor may securely collect (732) deposited currency 734 through a currency access panel 736.

In accordance with this aspect of the invention, the products 708 dispensed by the vending machine 700 include individually packaged volumetrically reduced absorbent articles, such as diapers. The products 708 additionally may include multi-packs of volumetrically reduced absorbent articles such as diapers; kits including volumetrically reduced absorbent articles such as diapers, toys containing volumetrically reduced absorbent articles such as diapers, and disguisedly packaged absorbent articles. Moreover, products 708 that do contain volumetrically reduced diapers each preferably contains one of the many embodiments of an individually vacuum-packed diaper as previously disclosed herein.

It is to be understood that the above referenced arrangements are illustrative of the application for the principles of the present invention. It will be apparent to those of ordinary skill in the art that numerous modifications can be made without departing from the principles and concepts of the invention as set forth in the claims.

What is claimed is:

1. An arrangement at a commercial establishment for facilitating the changing of a diaper of a child by a customer of the commercial establishment, the arrangement comprising:
   (a) a baby changing station mounted on a wall and having a baby changing platform; and
   (b) a vending machine mounted on a wall for dispensing a diaper, said vending machine comprising
      (i) at least one compartment for storing products for individual dispensing in response to selection by a consumer; and
      (ii) a plurality of products disposed within said at least one compartment for individually dispensing to consumers;
      (iii) wherein each of said plurality of products disposed within said at least one compartment includes therein a vacuum-packed diaper; and
      (iv) wherein said vending machine extends completely through said wall on which said vending machine is mounted and includes a posterior access panel for restocking of said products.

2. The arrangement of claim 1, wherein said wall on which said vending machine is mounted comprises a wall of a public restroom of the commercial establishment.

3. The arrangement of claim 1, wherein a said product disposed within said vending machine comprises a multi-pack of vacuum-packed diapers.

4. The arrangement of claim 1, wherein a said product disposed within said vending machine comprises a kits having therein a vacuum-packed diaper, said kit further including therein a diaper accessory.

5. The arrangement of claim 1, wherein a said product disposed within said vending machine comprises a disguisedly packaged vacuum-packed diaper.

6. The arrangement of claim 1, wherein said wall on which said vending machine is mounted and said wall on which said baby changing station is mounted comprise the same wall.

7. An arrangement at a commercial establishment for facilitating the changing of a diaper of a child by a customer of the commercial establishment, the arrangement comprising:
   (a) a baby changing station mounted on a wall and having a baby changing platform; and
   (b) a vending machine mounted on a wall for dispensing a diaper, said vending machine comprising,
      (i) at least one compartment for storing products for individual dispensing in response to selection by a consumer;
      (ii) a plurality of products disposed within said at least one compartment for individually dispensing to consumers; and
      (iii) a posterior access panel for removing deposited currency from said vending machine;
      (iv) wherein each of said plurality of products disposed within said at least one compartment includes therein a vacuum-packed diaper.

8. The arrangement of claim 7, wherein said wall on which said vending machine is mounted comprises a wall of a public restroom of the commercial establishment.

9. The arrangement of claim 7, wherein a said product disposed within said vending machine comprises a multi-pack of vacuum-packed diapers.

10. The arrangement of claim 7, wherein a said product disposed within said vending machine comprises a kit having therein a vacuum-packed diaper, said kit further including therein a diaper accessory.

11. The arrangement of claim 7, wherein a said product disposed within said vending machine comprises a disguisedly packaged vacuum-packed diaper.

12. The arrangement of claim 7, wherein said wall on which said vending machine is mounted and said wall on which said baby changing station is mounted comprise the same wall.

13. An arrangement at a commercial establishment for facilitating the changing of a diaper of a child by a customer of the commercial establishment, the arrangement comprising:
   (a) a baby changing station mounted on a wall and having a baby changing platform; and
   (b) a vending machine mounted on a wall for dispensing a diaper, said vending machine comprising,
      (i) at least one compartment for storing products for individual dispensing in response to selection by a consumer;
      (ii) a plurality of products disposed within said at least one compartment for individually dispensing to consumers; and
      (iii) a posterior access panel for removing deposited currency from said vending machine;
      (iv) wherein each of said plurality of products disposed within said at least one compartment includes therein a vacuum-packed diaper; and
      (v) wherein said vending machine extends completely through said wall on which said vending machine is mounted and includes a posterior access panel for restocking of said products.

14. The arrangement of claim 13, wherein said wall on which said vending machine is mounted comprises a wall of a public restroom of the commercial establishment.

15. The arrangement of claim 13, wherein a said product disposed within said vending machine comprises a multi-pack of vacuum-packed diapers.

16. The arrangement of claim 13, wherein a said product disposed within said vending machine comprises a kit having therein a vacuum-packed diaper, said kit further including therein a diaper accessory.

17. The arrangement of claim 13, wherein a said product disposed within said vending machine comprises a disguisedly packaged vacuum-packed diaper.

18. The arrangement of claim 13, wherein said wall on which said vending machine is mounted and said wall on which said baby changing station is mounted comprise the same wall.

* * * * *